United States Patent [19]

Mikoshiba et al.

[11] Patent Number: 5,223,380
[45] Date of Patent: Jun. 29, 1993

[54] COLOR DEVELOPING AGENT AND PROCESS FOR FORMING IMAGE

[75] Inventors: Hisashi Mikoshiba; Mitsugu Tanaka, both of Minami-ashigara, Japan

[73] Assignee: Fuji Photo Film Co., Ltd., Minami-ashigara, Japan

[21] Appl. No.: 855,657

[22] Filed: Mar. 23, 1992

Related U.S. Application Data

[63] Continuation-in-part of Ser. No. 699,661, May 14, 1991, abandoned.

[30] Foreign Application Priority Data

May 14, 1990 [JP] Japan .................. 2-123685

[51] Int. Cl.$^5$ ................................ G03C 7/30
[52] U.S. Cl. ...................... 430/435; 430/440; 430/446; 430/467
[58] Field of Search ............... 430/435, 439, 440, 441, 430/442, 446, 467

[56] References Cited

U.S. PATENT DOCUMENTS 4,636,460 1/1987 Meckl et al. .................. 430/442

FOREIGN PATENT DOCUMENTS 393523 10/1990 European Pat. Off. .
30333 3/1978 Japan .................. 430/442
4011255 1/1992 Japan .................. 430/467

Primary Examiner—Hoa Van Le
Attorney, Agent, or Firm—Burns, Doane, Swecker & Mathis

[57] ABSTRACT

A process for forming an image comprises color-developing an image-wise exposed silver halide color photographic photosensitive material in the presence of a p-phenylenediamine color developing agents such as

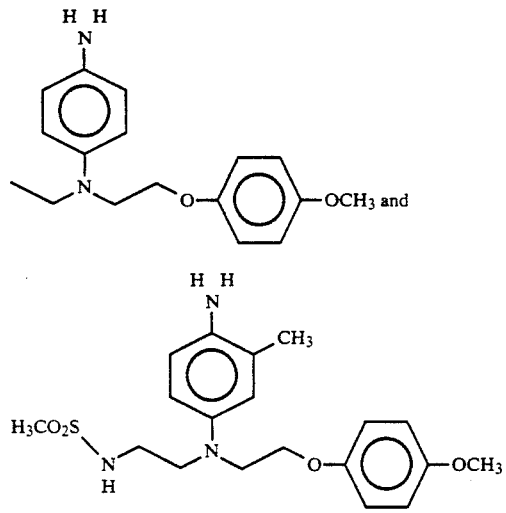

Due to the effect of the specific color-developing agent, there can be obtained an image having a quite high fastness to light.

13 Claims, No Drawings

COLOR DEVELOPING AGENT AND PROCESS FOR FORMING IMAGE

CROSS-REFERENCE TO RELATED APPLICATION

This application is a continuation-in-part of application Ser. No. 07/699,661, filed May 14, 1991, now abandoned, which is incorporated herein in its entirety by reference for all purposes.

BACKGROUND OF THE INVENTION

The present invention relates to a color developing agent for a silver halide color photographic photosensitive material and a process for forming an image with this color developing agent. In particular, the present invention relates to a p-phenylenediamine color developing agent capable of forming a color image in combination with a coupler, and a process for forming an image with this color developing agent.

A color photographic image is usually formed by processing a silver halide color photographic photosensitive material as shown below. The photosensitive material is first image-wise exposed and then developed with a developing composition comprising a developing agent. In this step, the silver halide is reduced into silver and the developing agent is oxidized. The thus-prepared oxide of the developing agent is coupled with the coupler to form an image-forming dye corresponding the developed silver. It is well-known that a p-phenylenediamine derivative is used as the color developing agent in order to obtain the color image, taking advantage of the oxidizing power of the exposed silver halide.

Regarding the p-phenylenediamine derivative, for example, alkyl groups at N-position proposed heretofore include N-hydroxyalkyl groups described in U.S. Pat. No. 2,108,243, N-sulfonamidoalkyl groups described in U.S. Pat. Nos. 2,193,015, 2,552,240 and 2,566,271, N-acylaminoalkyl groups described in U.S. Pat. Nos. 2,552,242 and 2,592,363, N-acylalkyl groups described in U.S. Pat. No. 2,374,337, N-alkoxyalkyl groups described in U.S. Pat. No. 2,603,656, Japanese Patent Unexamined Published Application (hereinafter referred to as "J.P. KOKAI") Nos. 47-11534 and 47-11535, Japanese Patent Publication for Opposition Purpose (hereinafter referred to as "J.P. KOKOKU") Nos. 54-16860, 58-14670 and 58-23618, N-sulfoalkyl groups described in British Patent No. 811,679 and N-aralkyl groups described in U.S. Pat. No. 2,716,132. The substituents of the benzene nucleus include, for example, nuclear alkoxyl groups described in U.S. Pat. No. 2,304,953, 2,548,574, 2,552,240 and 2,592,364, nuclear acylaminosulfonamido groups described in U.S. Pat. Nos. 2,350,109 and 2,449,919, nuclear acylaminoalkylsulfonamidoalkyl groups described in U.S. Pat. Nos. 2,552,241, 2,556,271 and 2,592,364, nuclear amino group described in U.S. Pat. Nos. 2,570,116, 2,575,027 and 2,652,331, and nuclear thiosulfonic acid groups described in British Patent No. 872,683. As for the use of compounds analogous to p-phenylenediamine as the color developing agents, tetrahydroquinolines and dihydroindoles are described in U.S. Pat. Nos. 2,196,739 and 2,556,259, N-(p-aminophenyl)hexamethyleneimines are described in U.S. Pat. No. 2,612,500 and 9-aminodurolidines are described in U.S. Pat. No. 2,707,681.

However, the conventional color developing agents have a problem in that the formed dye has yet an insufficient fastness. In particular, the fastness to light is relatively low and, therefore, it is difficult to keep the formed image as it is over a long period of time. Under these conditions, improvement of the storability of the image has eagerly been demanded.

Even though such an improvement has eagerly been demanded, investigations were scarcely made on color developing agents capable of forming a dye of a high fastness. Fastness of images was improved only by various techniques of inhibiting fading of the photosensitive materials.

Various processes are known such as a process wherein a coupler capable of forming a dye of a high fastness is used, a process wherein an ultraviolet ray-absorbing layer comprising an ultraviolet ray-absorber is used, a process wherein various fading inhibitors are used and a process wherein the state of the dye is improved so that the coupler is dispersed in a polymer.

If a color developing agent capable of forming a dye having a quite high fastness is developed, not only the image fastness is improved but also the development of a photosensitive material free from various additives which are essentially unnecessary such as an ultraviolet ray absorber and fading inhibitor is made possible. As a result, the thickness of the photosensitive material can be reduced, the sharpness can be improved and the rapid development is made possible. Further, the cost of the photosensitive material is reduced, since the additives become unnecessary. Thus, great merits can be obtained.

Particularly, photosensitive materials for color prints are usually exposed to a light more often than those for photosensitive materials for taking a picture such as color negative film, and improvement in the fastness of the image is a big theme of investigations. In the photosensitive materials for color printing now available on the market, the fastness of the image is improved by total effects obtained by combination of all the fading-inhibition techniques described above. However, by this fact, the freeness of the formulation of the photosensitive material is restricted. If a color developing agent capable of forming a dye of a quite high fastness is developed, the photosensitive material can be formulated without necessitating any taking of the fastness of the image into consideration and, therefore, freeness of the formulation is increased. For example, a photosensitive material having a remarkably improved coloring property can be thus formulated.

SUMMARY OF THE INVENTION

A primary object of the present invention is to provide a color developing agent capable of forming a dye of a high fastness of color development reactions.

Another object of the present invention is to provide a color developing agent to be contained in a color developing composition or photosensitive material to form an image of a high fastness.

Another object of the present invention is to provide a silver halide photosensitive material capable of forming an image having a remarkably improved fastness or a process for forming the image.

Another object of the present invention is to provide a silver halide photosensitive material of a low cost or process for forming an image at a low cost.

These and other objects of the present invention will be apparent from the description of this specification and Example.

The above-described objects of the present invention can be attained by a specific p-phenylenediamine color developing agent represented by the following general formula (I):

$$A\text{—}(\text{—}L\text{—}B)_q \qquad (I)$$

wherein A represents a p-phenylenediamine color developing agent residue, L represents a divalent connecting group or a mere bond, B represents an atomic group capable of inhibiting fading of a dye formed by the color development reaction of the p-phenylenediamine color developing agent of the formula (I) with a coupler compound, q represent an integer of 1 to 3, and when q is 2 or 3, L—B may be the same or different from one another.

Another aspect of the present invention relates to a process for forming an image, characterized in that a silver halide color photographic photosensitive material is color-developed in the presence of a p-phenylenediamine color developing agent represented by the above-described formula (I).

DESCRIPTION OF THE PREFERRED EMBODIMENTS

Detailed description will be made on the general formula (I):

A represents a p-phenylenediamine color developing agent residue and is preferably that represented by the following general formula (II):

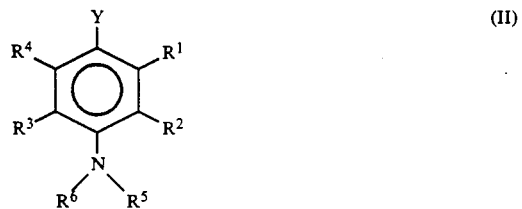

wherein $R^1$, $R^2$, $R^3$ and $R^4$ may be the same or different from one another and each represent a hydrogen atom or a non-metallic substituent. They preferably represent a hydrogen atom, halogen atom, amino group, alkyl group, aryl group, heterocyclic group, cyano group, nitro group, hydroxyl group, carboxyl group, alkoxyl group, aryloxy group, acylamino group, alkylamino group, anilino group, ureido group, sulfamoylamino group, alkylthio group, arylthio group, alkoxycarbonylamino group, sulfonamido group, carbamoyl group, sulfamoyl group, sulfonyl group, alkoxycarbonyl group, heterocyclicoxy group, azo group, acyloxy group, carbamoyloxy group, silyl group, silyloxy group, aryloxycarbonylamino group, imido group, heterocyclic thio group, sulfinyl group, phosphonyl group, sulfo group, aryloxycarbonyl group or acyl group.

In particular, they each represent a hydrogen atom, halogen atom (such as fluorine or chlorine atom), amino group having 0 to 8 carbon atoms (such as diethylamino group), straight, branches, or cyclic alkyl group having 1 to 16 carbon atoms which may be substituted with an alkenyl, alkynyl, hydroxyl, nitro or cyano group, with a halogen atom or a substituent connected therewith through an oxygen, nitrogen or sulfur atom or through a carbonyl group (such as methyl, ethyl, propyl, isopropyl, t-butyl, 2-hydroxyethyl, 3-hydroxypropyl, 2-methanesulfonamidoethyl, 3-methanesulfonamidopropyl, 2-methanesulfonylethyl, 2-methoxyethyl, cyclopentyl, 2-acetamidoethyl, 2-carboxylethyl, 2-carbamoylethyl, 3-carbamoylpropyl, n-hexyl, 2-hydroxypropyl, 4-hydroxybutyl, 2-carbamoylaminoethyl, 3-carbamoylaminopropyl, 4-carbamoylaminobutyl, 4-carbamoylbutyl, 2-carbamoyl(1-methyl)ethyl and 4-nitrobutyl groups, aryl groups, (such as phenyl, naphthyl and p-methoxyphenyl groups), heterocyclic groups (such as 2-furyl, 2-thienyl, 2-pyrimidinyl, 2-benzotriazolyl, imidazolyl and pyrazolyl groups), cyano group, nitro group, hydroxyl group, carboxyl group, alkoxyl groups (such as methoxy, ethoxy, 2-methoxyethoxy and 2-methanesulfonylethoxy groups), aryloxy groups (such as phenoxy group), acylamino groups (such as acetamido and 2-methoxypropionamido groups), alkylamino groups (such as dimethylamino and diethylamino groups), anilino groups (such as anilino and m-nitroanilino groups), ureido groups (such as methylureido and N,N-diethylureido groups), sulfamoylamino groups (such as dimethylsulfamoylamino group), alkythio groups (such as methylthio and ethylthio groups), arylthio groups (such as phenylthio group), alkoxycarbonylamino groups (such as methoxycarbonylamino and ethoxycarbonylamino groups), sulfonamido groups (such as methanesulfonamido group), carbamoyl groups (such as N,N-dimethylcarbamoyl and N-ethylcarbamoyl groups), sulfamoyl groups (such as dimethylsulfamoyl group), sulfonyl groups (such as methanesulfonyl and ethanesulfonyl groups), alkoxycarbonyl groups (such as methoxycarbonyl and ethoxycarbonyl groups), heterocyclic oxy groups (such as 1-phenyltetrazol-5-oxy and 2-tetrahydropyranyloxy groups), azo groups (such as phenylazo and 2-hydroxy-4-propanoylphenylazo groups), acyloxy groups (such as acetoxy group), carbamoyloxy groups (such as N,N-dimethylcarbamoyloxy group), silyl groups (such as trimethylsilyl group), silyloxy groups (such as trimethylsilyloxy group), aryloxycarbonylamino groups (such as phenoxycarbonylamino group), imido groups (such as N-succinimide group), heterocyclic thio groups (such as 2-benzothiazolylthio and 2-pyridylthio groups), sulfinyl groups (such as ethanesulfinyl group), phosphonyl groups (such as methoxyphosphonyl group), sulfo group, aryloxycarbonyl groups (such as phenoxycarbonyl group) and acyl groups (such as acetyl and benzoyl groups).

Among these substituents, preferred $R^1$, $R^2$, $R^3$ and $R^4$ include hydrogen atom, and alkyl, alkoxy, alkoxycarbonylamino and ureido groups. In particular, $R^1$ is preferably a hydrogen atom or alkyl, alkoxyl, alkoxycarbonylamino or ureido group, and $R^2$, $R^3$ and $R^4$ are preferably each hydrogen atom.

$R^5$ and $R^6$ which may be the same or different are preferably each a hydrogen atom or an alkyl, aryl or heterocyclic group.

In particular, examples of $R^5$ and $R^6$ include a hydrogen atom, straight-chain, branched or cyclic alkyl groups having 1 to 6 carbon atoms which may be substituted with an alkenyl, alkynyl, hydroxyl, nitro, cyano group or a halogen atom or a substituent connected therewith through an oxygen, nitrogen or sulfur atom or through a carbonyl group (for example, methyl, ethyl, propyl, isopropyl, t-butyl, 2-hydroxyethyl, 3-hydroxypropyl, 2-methanesulfonamidoethyl, 3-methanesulfonamidopropyl, 2-methanesulfonylethyl, 2-methoxyethyl, cyclopentyl, 2-acetoamidoethyl, 2-carboxylethyl, 2-carbamoylethyl, 3-carbamoylpropyl, n-hexyl, 2-hydroxypropyl, 4-hydroxybutyl, benzyl, 2-carbamoylaminoethyl, 3-carbamoylaminopropyl, 4-carbamoylaminobutyl, 4-carbamoylbutyl, 2-carbamoyl(1-methyl)ethyl and 4-nitrobutyl groups), aryl groups having 6 to 12 carbon atoms (such as phenyl, p-tolyl and m-chlorophenyl groups) and heterocyclic groups having 3 to 10 carbon atoms (such as

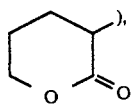

$R^5$ and $R^6$ are each particularly preferably a substituted or unsubstituted alkyl group having 1 to 16 carbon atoms.

$R^1$ and $R^2$ and/or $R^2$ and $R^5$ and/or $R^5$ and $R^6$ and/or $R^3$ and $R^6$ and/or $R^3$ and $R^4$ may be bonded together to form a ring structure.

Y represents $-NH_2$, $-NHY^1$ or $-N=Y^2$, $Y^1$ represents $-SO_3H$, $-SO_3Na$, $-SO_2-R^{21}$,

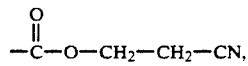

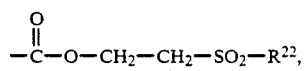

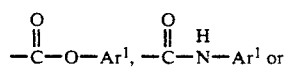

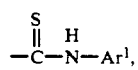

$R^{21}$ and $R^{22}$ may be the same or different and each represent an alkyl group or aryl group. $Ar^1$ represents an aryl group.

$Y^2$ represents

$Ar^2$ represents an aryl group.

Examples of $R^{21}$ and $R^{22}$ include alkyl groups having 1 to 10 carbon atoms (such as methyl, ethyl and isopropyl groups) and aryl groups having 6 to 12 carbon atoms (such as phenyl, p-tolyl and o-chlorophenyl groups).

The aryl groups represented by $Ar^1$ and $Ar^2$ may be either unsubstituted or substituted. The substituents of the aryl groups may be any possible substituents. They are preferably hydroxyl, amino, alkoxyl, aminocarbonylamino, alkyl, acylamino, sulfonamido, alkoxycarbonylamino, sulfonyl, carbamoyl, sulfamoyl and cyano groups, halogen atoms, and alkoxycarbonyl, acyl, acyloxy, sulfonic acid and carboxyl groups. These substituents may be further substituted.

When A of the formula (I) is represented by the general formula (II), B of the formula (I) is bonded with A through $R^1$, $R^2$, $R^3$, $R^4$, $R^5$ or $R^6$ and also through L.

Where a color developing agent is covalently bonded to an atomic group capable of inhibiting fading of dye, a dye formed by the color developing reaction of the thus prepared color developing agent with a coupler compound has the atomic group capable of inhibiting fading of dye in its molecule, so that the fading of the formed dye can be greatly inhibited due to the atomic group without incorporating a fading inhibitor into silver halide color photographic materials before the color development.

Now, the detailed description will be made on B.

B represents an atomic group capable of inhibiting fading of a dye formed by the color development reaction of the p-phenylenediamine color developing agent of the formula (I) with a coupler compound.

The effects of inhibiting fading may be any effects by which the fading is eventually inhibited. They are, for example, ultraviolet ray-absorbing effect, automatic oxidation inhibition effect, single state oxygen quenching effect, superoxide quencher effect, peroxide decomposition effect, radical quencher effect and dye-excited state quencher effect. Further, these effects may be also those of various fading inhibitors known to have an effect of inhibiting the fading of dyes, though the mechanism thereof has not yet been known. The term "fading" herein indicates reduction of the image density due to one or more of light, heat, water, etc.

Among the atomic groups represented by B, preferred are those of the following general formula (III):

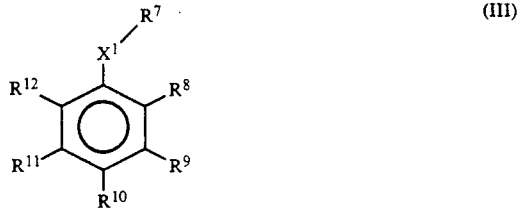

(III)

wherein $R^7$ represents a nonmetallic substituent, i.e., a group which cannot be hydrolyzed such as a hydrogen atom or an alkyl, alkenyl, aryl, heterocyclic, silyl, acyl, sulfonyl or aminocarbonyl group, or a hydrolyzable group such as a phosphino or oxazalyl group, $X^1$ represents $-O-$, $-S-$ or $-NR^{13}-$, $R^{13}$ being a hydrogen atom or an alkyl or aryl group; $R^8$, $R^9$, $R^{10}$, $R^{11}$ and $R^{12}$ each represents a hydrogen atom or a non-metallic substituent, and among the substituents $X^1-R^7$, $R^8$, $R^9$, $R^{10}$, $R^{11}$ and $R^{12}$, two substituents arranged at o-position with each other may be bonded together to form a ring structure.

A of the formula (I) is bonded with B through $R^7$, $R^8$, $R^9$, $R^{10}$, $R^{11}$ or $R^{12}$ and also through L.

The detailed description will be made on the formula (III).

$R^7$ preferably represents a hydrogen atom, alkyl group having 1 to 6 carbon atoms (such as methyl, ethyl, n-propyl, isopropyl, methoxyethyl, t-butyl, phenoxyethyl or cyanoethyl group), alkenyl group having 3 to 7 carbon atoms (such as allyl, homoallyl, crotyl, prenyl or geranyl group), aryl group having 6 to 12 carbon atoms (such as phenyl p-chlorophenyl or naphthyl group), heterocyclic group having 3 to 10 carbon atoms (such as

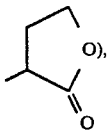

silyl group having 3 to 15 carbon atoms (such as trimethylsilyl or t-butyldimethylsilyl group) or phosphino group having 1 to 12 carbon atoms.

Among them, $R^7$ is preferably a hydrogen atom or an alkyl or aryl group.

$R^7$ is particularly preferable an alkyl group.

$X^1$ represents —O—, —S— or —NR$^{13}$.

$R^{13}$ is preferably a hydrogen atom, an alkyl group having 1 to 6 carbon atoms (such as methyl, ethyl, n-propyl, isopropyl, methoxyethyl or cyanoethyl group) or aryl group having 6 to 12 carbon atoms (such as phenyl, p-chlorophenyl or p-methoxyphenyl group).

Among them, $X^1$ is preferably —O—.

$R^8$, $R^9$, $R^{10}$, $R^{11}$ and $R^{12}$ are each preferably a hydrogen atom. —$X^1$—$R^7$, alkyl, alkenyl, aryl, aryloxycarbonyl or alkoxycarbonyl group, halogen atom or acyl, sulfonyl, carbamoyl, acylamino, sulfamoyl, cyano, nitro, sulfo or carboxyl group.

Among them, $R^8$, $R^9$, $R^{10}$, $R^{11}$ and $R^{12}$ are each preferably a hydrogen atom, —O—$R^7$, —S—$R^7$, —NR$^{13}$R$^7$ ($R^{13}$ and $R^7$ may be bonded together to form a ring structure), alkyl group having 1 to 6 carbon atoms (such as methyl, ethyl or t-butyl group), halogen atom (such as F or Cl), acyl group having 2 to 6 carbon atoms (such as acetyl group), acylamino group having 1 to 6 carbon atoms (such as acetylamino group) or alkoxycarbonyl group having 2 to 6 carbon atoms (such as methoxycarbonyl group).

It is preferable that $X^1$ be —O— or —NR$^{13}$— in view of fading inhibition ability. It is also preferably that $R^8$, $R^9$, $R^{10}$, $R^{11}$ and $R^{12}$ be each a hydrogen atom, alkyl, alkenyl, aryl, aryloxycarbonyl or alkoxycarbonyl group, provided that at least one of $R^8$ and $R^{10}$ is —$X^1$—$R^7$ ($X^1$ is —O— or —NR$^{13}$—), $R^7$ is an alkyl and $R^{13}$ is a hydrogen or alkyl.

Most preferably, $X^1$ represents —O— and $R^1$ represents an alkyl group having 1 to 6 carbon atoms and at least one of $R^8$, $R^{10}$, and $R^{12}$ represents —O—$R^7$ ($R^7$ being an alkyl group having 1 to 6 carbon atoms).

In another example of the most preferred structure, $R^8$ and $R^{12}$ are each an alkyl group having 1 to 6 carbon atoms and $X^1$—$R^7$ is —OH.

Another preferred structure of the atomic group B is represented by the following general formula (IV):

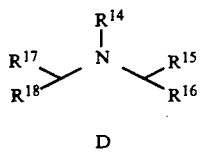

(IV)

wherein $R^{14}$ represents a hydrogen atom or alkyl, alkenyl, aryl, hydroxyl, acyl, sulfonyl or sulfinyl group, $R^{15}$, $R^{16}$, $R^{17}$ and $R^{18}$ may be the same or different from one another and each represent a hydrogen atom, alkyl group or aryl group, and D represents a non-metallic atomic group necessitated for forming a 5- to 7-membered ring.

A is bonded to B through $R^{14}$, $R^{15}$, $R^{16}$, $R^{17}$, $R^{18}$, D and through L.

The detailed description will be made on the formula (IV):

$R^{14}$ is preferably a hydrogen atom, alkyl group having 1 to 6 carbon atoms (such as methyl, ethyl, t-butyl, methoxyethyl or cyanoethyl group), alkenyl group having 3 to 7 carbon atoms (such as allyl, homoallyl, crotyl, prenyl or geranyl group), aryl group having 6 to 12 carbon atoms (such as phenyl, p-chlorophenyl or naphthyl group), hydroxyl group, acyl group having 2 to 6 carbon atoms (such as acetyl, propionyl or pivaloyl group), sulfonyl group having 1 to 7 carbon atoms (such as methanesulfonyl or p-toluenesulfonyl group) or sulfinyl group having 1 to 7 carbon atoms (such as methanesulfinyl group).

Among them, hydrogen atom or the alkyl group is particularly preferred. The most preferred is an alkyl group. $R^{15}$, $R^{16}$, $R^{17}$ and $R^{18}$ may be the same or different and preferably each represent a hydrogen atom, alkyl group having 1 to 6 carbon atoms (such as methyl, ethyl, t-butyl or isopropyl group) or aryl group having 6 to 10 carbon atoms (such as phenyl group). Among them, an alkyl group having 1 to 4 carbon atoms is particularly preferred.

D preferably forms a structure of the following formula (V), (VI) or (VII) together with the atomic group with which it is bonded:

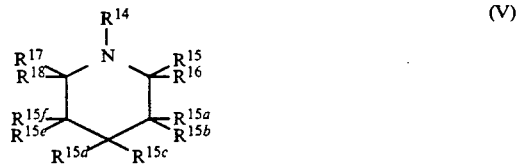

(V)

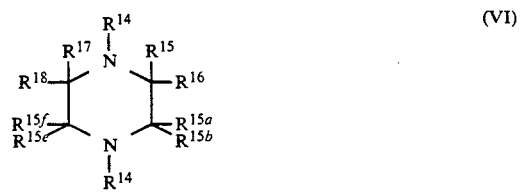

(VI)

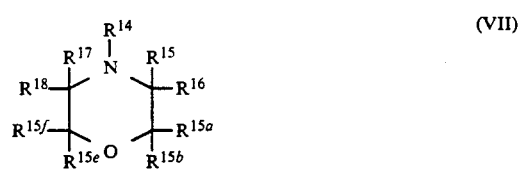

(VII)

wherein $R^{15a}$, $R^{15b}$, $R^{15c}$, $R^{15d}$, $R^{15e}$ and $R^{15f}$ may be the same or different from one another and each represent a hydrogen atom or a nonmetallic substituent.

Preferred examples of them include hydrogen atom, alkyl groups having 1 to 6 carbon atoms (such as methyl, ethyl, isopropyl, n-propyl, t-butyl, methoxyethyl and cyanoethyl groups), hydroxyl group, alkoxy groups having 1 to 6 carbon atoms (such as methoxy, ethoxy, t-butoxy, isopropoxy, allyloxy and methoxyethoxy groups), acyloxy groups having 1 to 6 carbon atoms (such as acetyloxy and pivaloyloxy groups), alkylamino groups having 1 to 6 carbon atoms (such as methylamino, dimethylamino, ethylamino and diethylamino groups), and arylamino groups having 6 to 10 carbon atoms (such as anilino and p-chloranilino groups) and sulfonamido groups having 1 to 6 carbon atoms (such as methanesulfonylamino group).

Among them, hydrogen atom or alkyl groups are particularly preferred.

$R^{14}$ is the same as $R^{14}$. Preferred examples thereof are the same as those of $R^{14}$.

Adjacent two of $R^{15}$, $R^{16}$, $R^{15a}$, $R^{15b}$, $R^{15c}$, $R^{15d}$, $R^{15e}$, $R^{15f}$, $R^{17}$ and $R^{18}$ may be bonded together to form a ring structure.

When B of the formula (I) has a structure shown by the formula (V), (VI) or (VII), A of the formula (I) is bonded therewith through L and $R^{14}$, $R^{15}$, $R^{16}$, $R^{17}$, $R^{18}$, $R^{15a}$, $R^{15b}$, $R^{15c}$, $R^{15d}$, $R^{15e}$ or $R^{15f}$.

The more detailed description will be made on B of the general formula (I).

As described above, the structure of B is preferably that represented by the formula (III), (IV), (V), (VI) or (VII). However, the fading-inhibition effects of the five structures are not equivalent to one another. In particular, the structure of the formula (III) exhibits a remarkable effect of inhibiting fading of a dye formed from a magenta coupler comprising a pyrazolotriazole or pyrazolone compound.

Therefore, when the magenta dye-forming layer of the photosensitive material contains no fading inhibitor or it contains only a reduced amount of such an inhibitor, B has preferably a structure of the formula (III).

The compounds of the present invention have a relatively large number of carbon atoms in their structures and when they have no water-soluble group at all, they are difficultly soluble in the processing solution.

Accordingly, when the compounds have more than 24 carbon atoms, they preferably have at least one water-soluble group. The watersoluble groups include, for example, hydroxyl, sulfo, sulfonylamino, hydroxycarbonyl, carbamoyl and sulfamoyl groups.

When a high fastness is required of the formed dye, q is preferably 2 or 3.

When a high development reaction rate is required, a compound of the present invention having a low molecular weight is preferably used in order to facilitate the diffusion of the compound. In such a case, q is preferably 1.

Under actual conditions, a compound of the formula wherein q is 1 is more preferred than that where q is 2 or 3.

Examples of the structures B of the formula (I) will be given below, which by no means limit the invention:

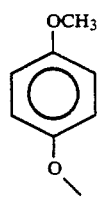

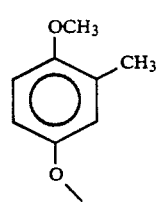

-continued

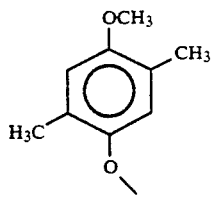

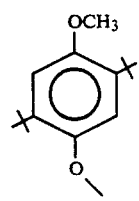

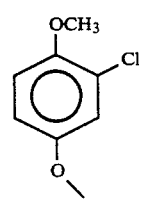

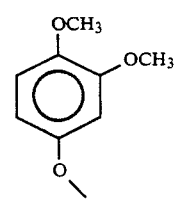

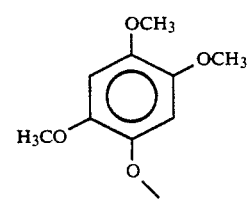

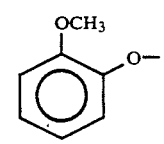

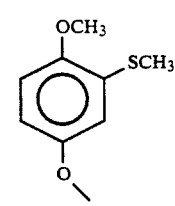

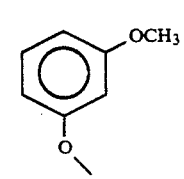

-continued
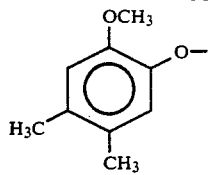
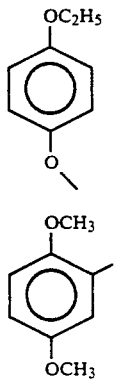
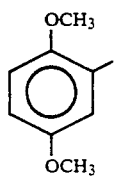
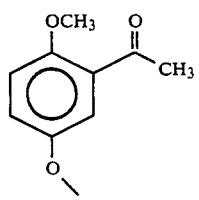
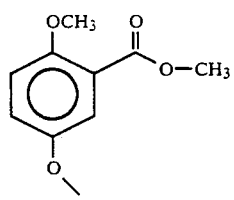
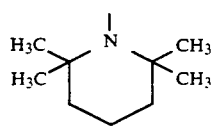
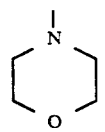
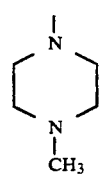
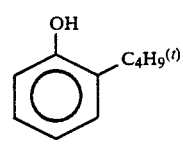
-continued
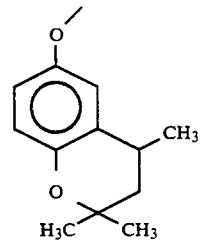
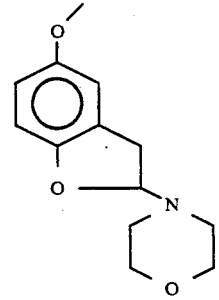
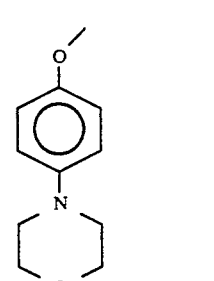
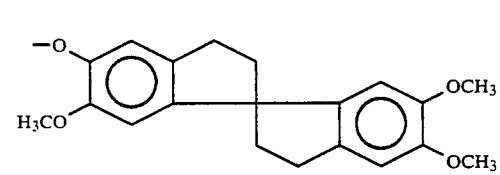
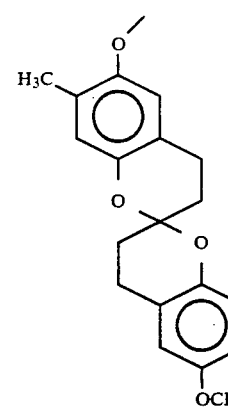
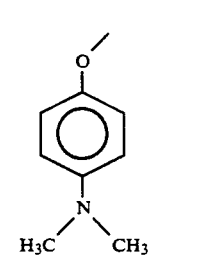

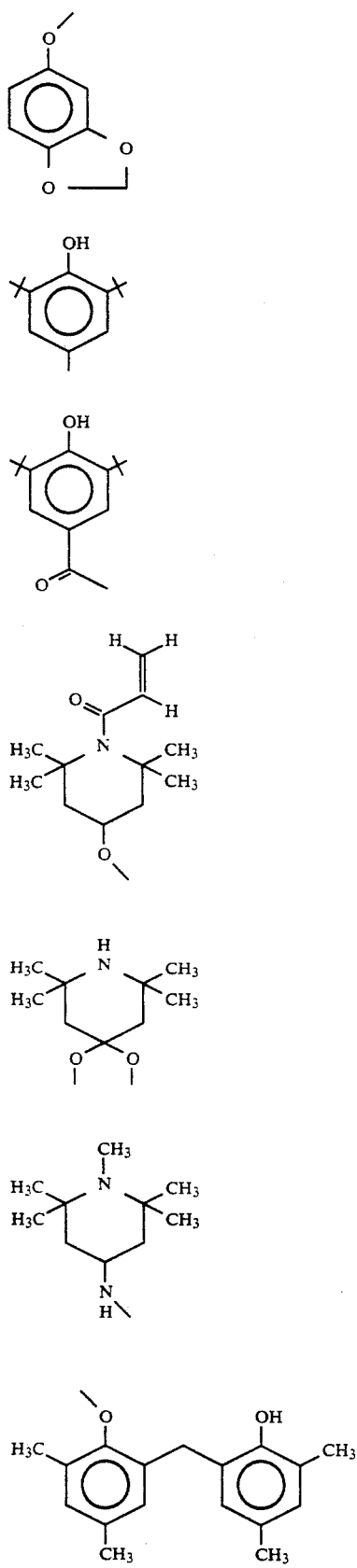
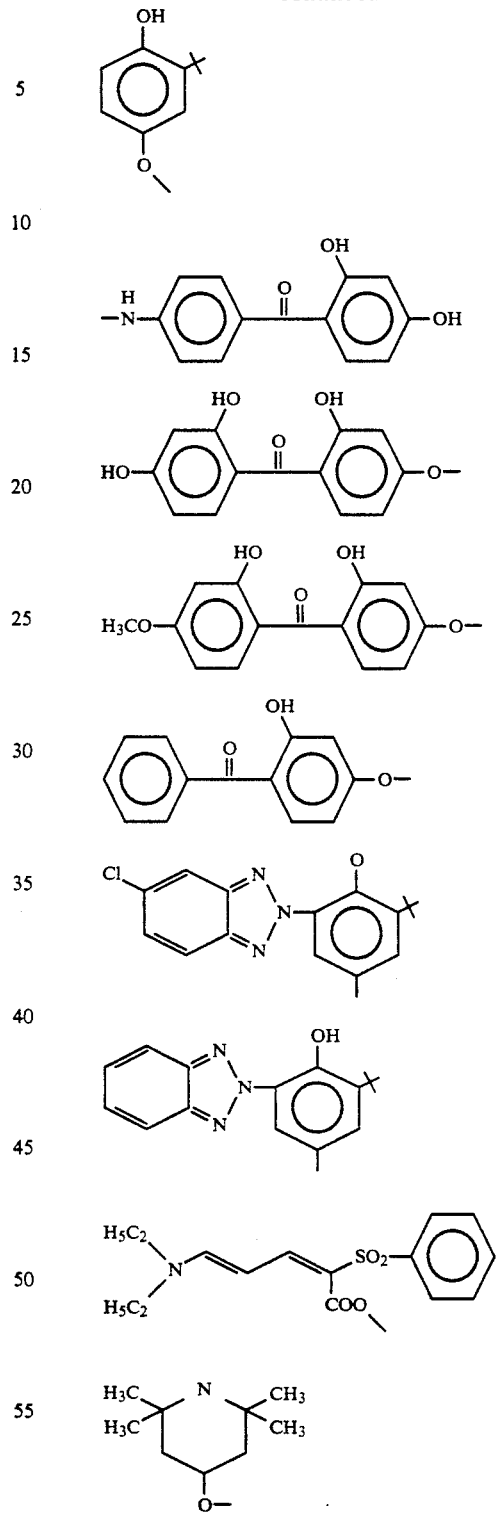

It is preferable that the connecting group represented by L in the formula (I) be —NR¹⁹— group ($R^{19}$ is a hydrogen atom, alkyl group or aryl group), —SO₂— group, —CO— group, substituted or unsubstituted alkylene group, substituted or unsubstituted phenylene group, substituted or unsubstituted naphthylene group, —O— group, —SO— group and a group which is a combination of two or more groups mentioned above.

Among these, more preferable one is $-NR^{19}-SO_2-$, $-NR^{19}-CO-$, $-R^{20}-(L')_k-(R^{21})_l-$, wherein $R^{20}$ and $R^{21}$ each represent alkylene group, phenylene group, naphthylene group, L' represents $-O-$, $-CO-$, $-SO-$, $-SO_2-$, $SO_2NH-$, $-NHSO_2-$, $-CONH-$, $-NHCO-$, k represents an integer of 0 or 1, l is 1 where k is 1, and l is 1 or 0 where k is 0. Furthermore, groups in which $-NR^{19}-SO_2-$ or $-NR^{19}-CO-$ is combined with $-R^{20}-(L')_k-(R^{21})_l-$.

Preferable examples of $R^{19}$ include a hydrogen atom and alkyl group having 1 to 6 carbon atoms.

Preferable examples of $R^{20}$ and $R^{21}$ include alkylene group having 1 to 6 carbon atoms which may have a substituent such as alkyl group, alkoxy, hydroxy, halogen, cyano and the like, phenylene group which may be ortho, metha or para, and which may have a substituent such as alkyl, alcoxy, halogen, hydroxy, carboxyl, sulfamoyl, alkylsulfonylamino, sulfamide and the like, and naphthylene group which may have a substituent as mentioned in phenylene group.

On the other hand, $L^1$ shown below may be the same as those described in L, but is preferably a substituted to unsubstituted alkylene group having 1 to 8 carbon atoms.

Among the new developing agents of the present invention, those represented by the following formulae (XI) to (XIII) are more preferable.

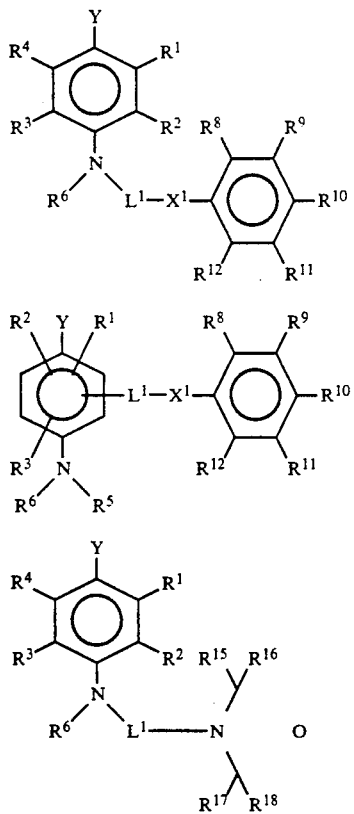

(XI)

(XII)

(XIII)

wherein $R^1$, $R^2$, $R^3$ and $R^4$ each represent a hydrogen atom, halogen atom, amino group, alkyl group, aryl group, heterocyclic group, cyano group, nitro group, hydroxyl group, carboxyl group, alkoxyl group, aryloxy group, acylamino group, alkylamino group, anilino group, ureido group, sulfamoylamino group, alkythio group, arylthio group, alkoxycarbonylamino group, sulfonamido group, carbamoyl group, sulfamoyl group, sulfonyl group, alkoxycarbonyl group, heterocyclicoxy group, azo group, acyloxy group, carbamoyloxy group, silyl group, silyloxy group, aryloxycarbonylamino group, imido group, heterocyclic thio group, sulfinyl group, phosphonyl group, sulfo group, aryloxycarbonyl group or acyl group, $R^5$ and $R^6$ represents a hydrogen atom or an alkyl, aryl or heterocyclic group, $X^1$ is $-O-$, $R^8$, $R^9$, $R^{10}$, $R^{11}$ and $R^{12}$ are each a hydrogen atom, $-X^1-R^7$ ($R^7$ is a hydrogen atom or an alkyl or aryl group), alkyl, alkenyl, aryl, aryloxycarbonyl or alkoxycarbonyl group, halogen atom or acyl, sulfonyl, carbamoyl, acylamino, sulfamoyl, cyano, nitro, sulfo or carboxyl group, and $L^1$ represents a substituted or unsubstituted alkylene group having 1 to 8 carbon atoms, and Y represents $-NH_2$, $-NHY^1$ or $-N=Y^2$, $Y^1$ represents $-SO_3H$, $-SO_3Na$, $-SO_2-R^{21}$,

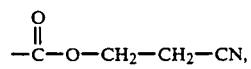

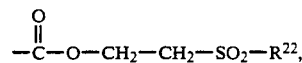

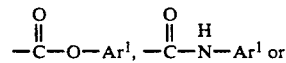

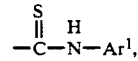

$R^{21}$ and $R^{22}$ may be the same or different and each represent an alkyl group or aryl group. $Ar^1$ represents an aryl group, $Y^2$ represents

and $Ar^2$ represents an aryl group, and $R^{15}$, $R^{16}$, $R^{17}$ and $R^{18}$ may be the same or different from one another and each represent a hydrogen atom, alkyl group or aryl group, D represents a non-metallic atomic group necessitated for forming a 5- to 7-membered ring.

The new developing agent of the present invention in the developer is used in the form of the free base or an organic or inorganic acid salt. Preferred organic acids include oxalic, methanesulfonic, benzenesulfonic, p-toluenesulfonic and 1,5-naphthalenedisulfonic acids. Preferred inorganic acids include hydrochloric, sulfuric and perchloric acids.

When the new developing agent of the present invention is incorporated into the photosensitive material, it is used in the form of the free developing agent or a salt thereof with an organic or inorganic acid. If necessary, it is used in the form of its precursor.

When the developing agent of the present invention is dissolved in the developer, Y preferably has a structure represented by the formula: $-NH_2$. When it is incorporated into the photosensitive material, it preferably has a precursor structure wherein Y represents $-NHY^1$ or $-N=Y^2$.

Examples of the developing agents of the present invention will be given below in the form of free bases, which by no means limit the present invention.
They are given herein in a simple manner such as
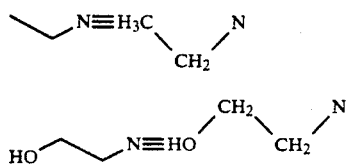
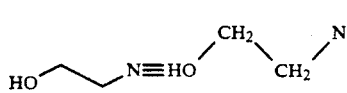
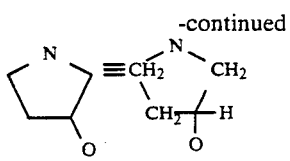
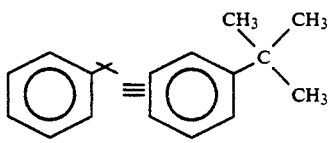
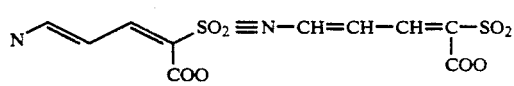
Examples of compounds:
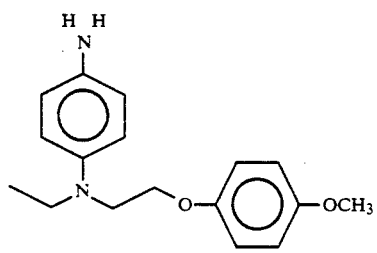
1
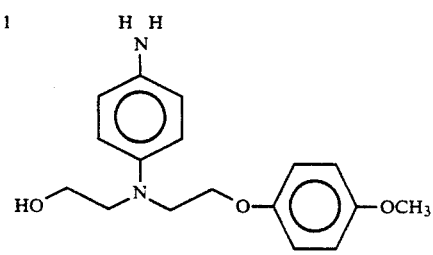
2
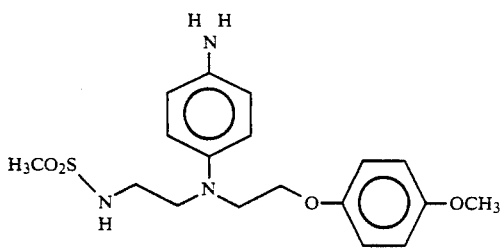
3
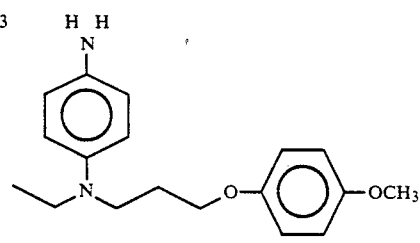
4
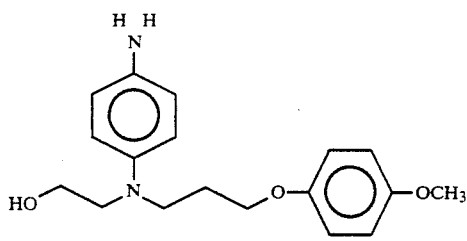
5
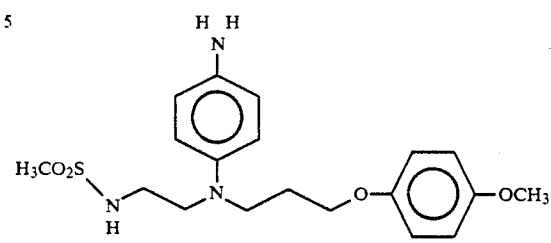
6
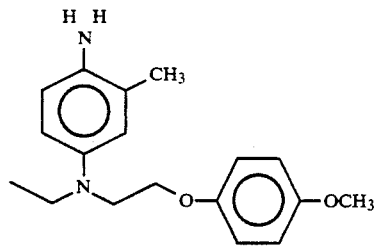
7
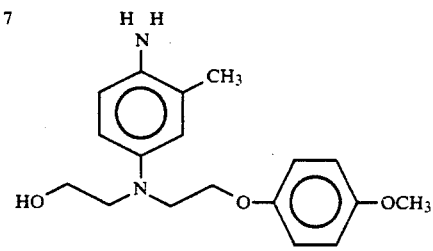
8
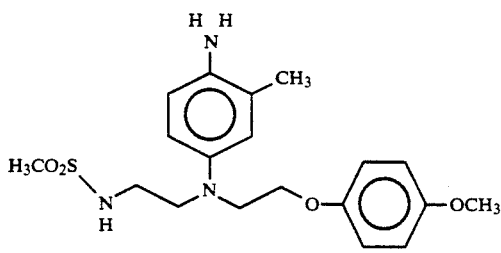
9
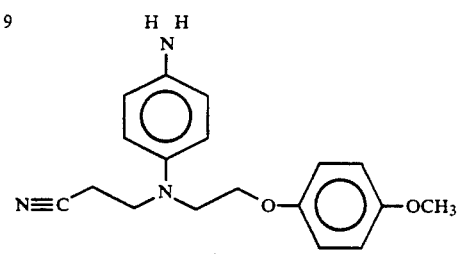
10

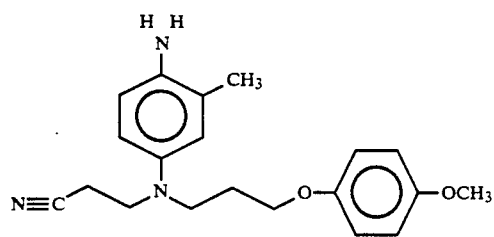
11
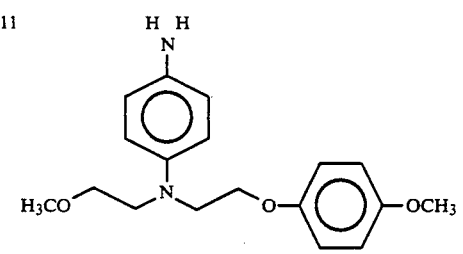
12
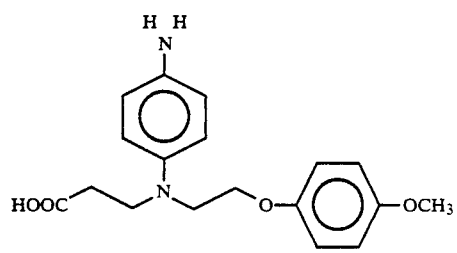
13
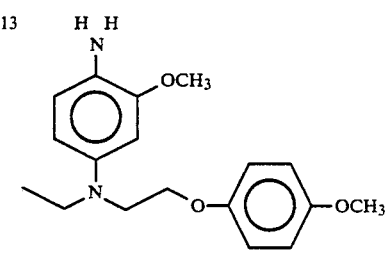
14
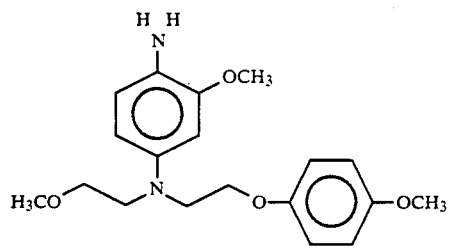
15
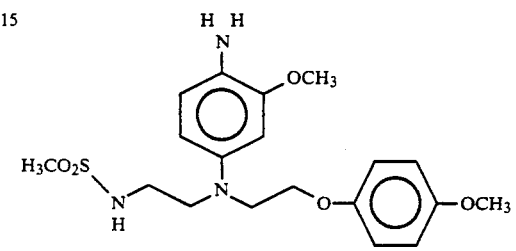
16
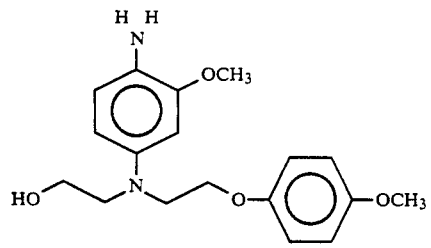
17
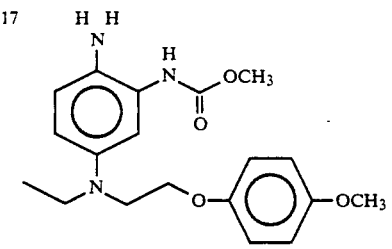
18
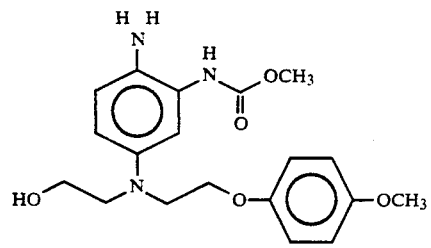
19
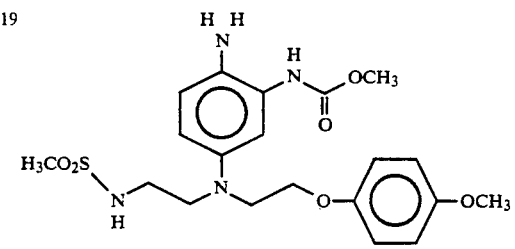
20
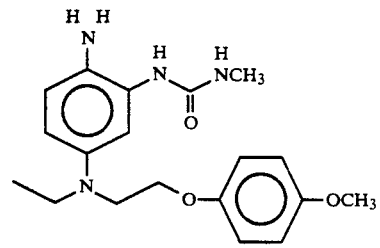
21
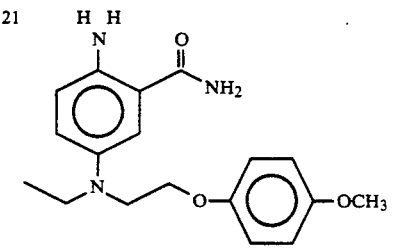
22

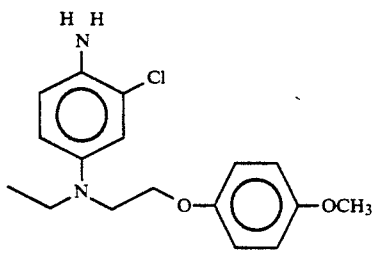
23
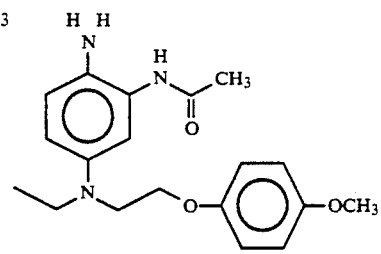
24
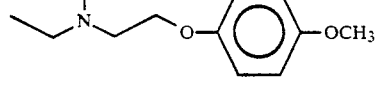
25
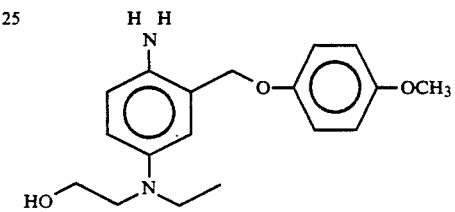
26
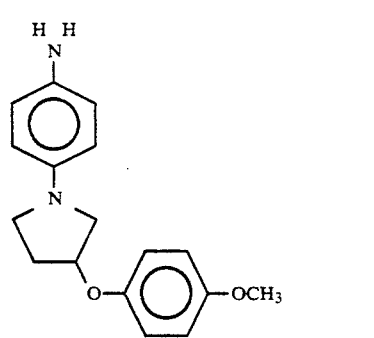
27
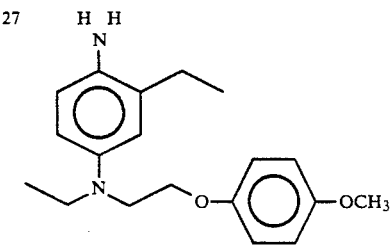
28
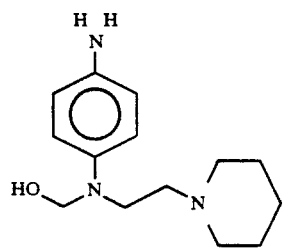
29
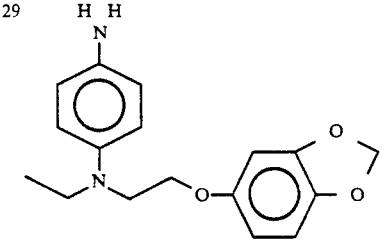
30
31
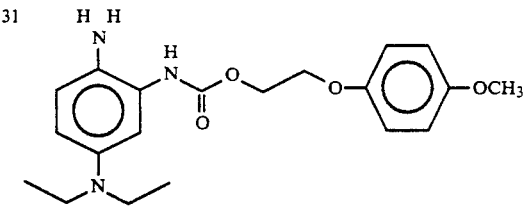
32
33
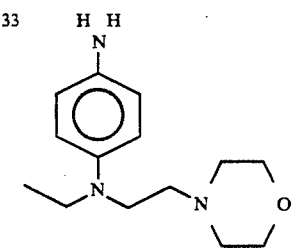
34

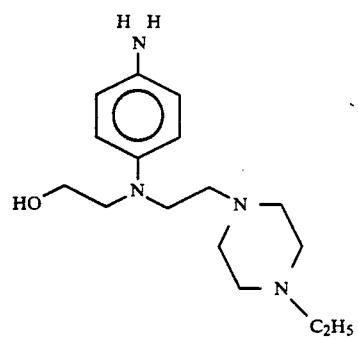
35
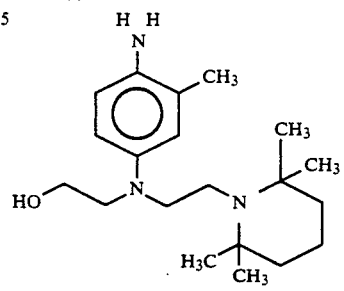
36
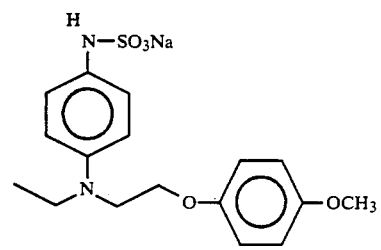
37
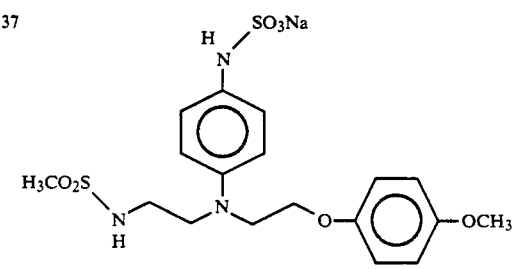
38
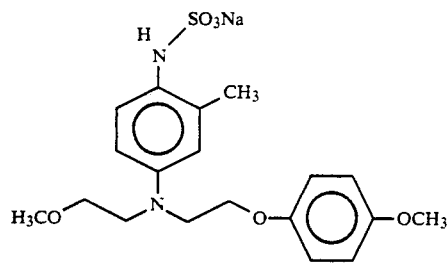
39
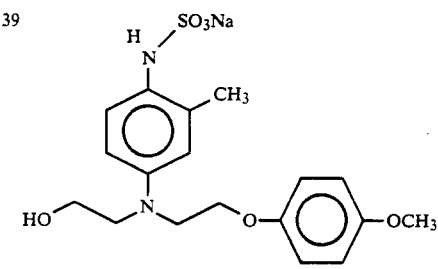
40
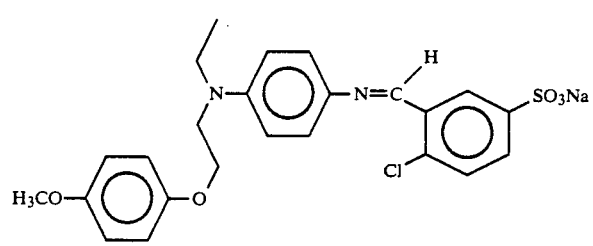
41
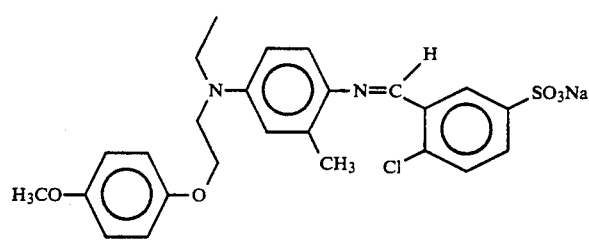
42
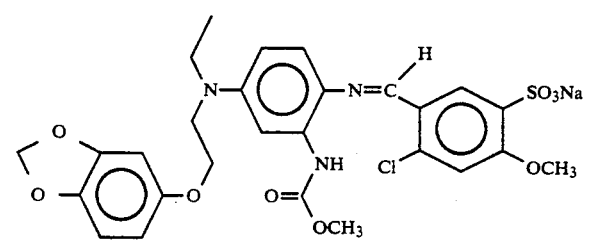
43

-continued
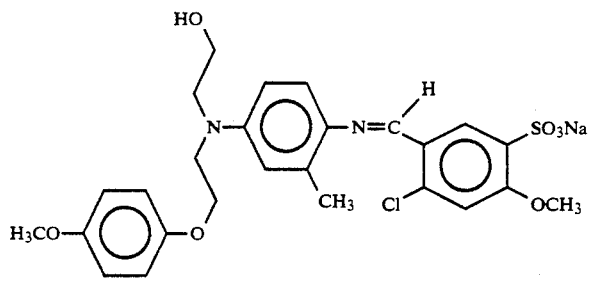
44
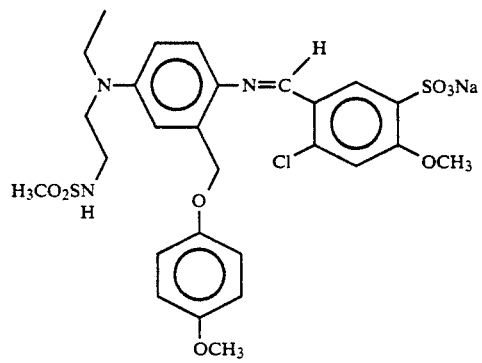
45
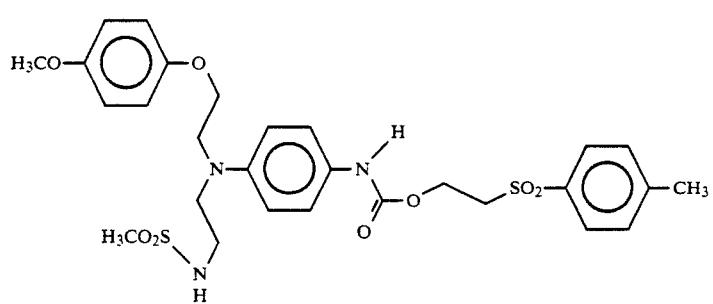
46
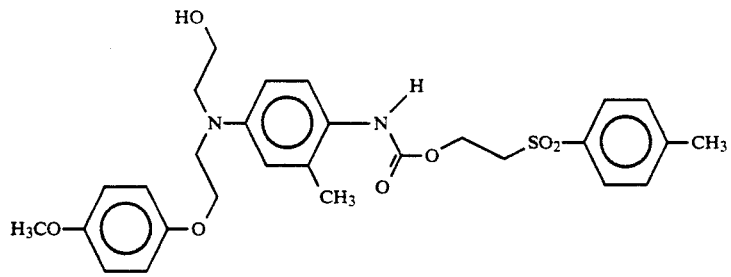
47
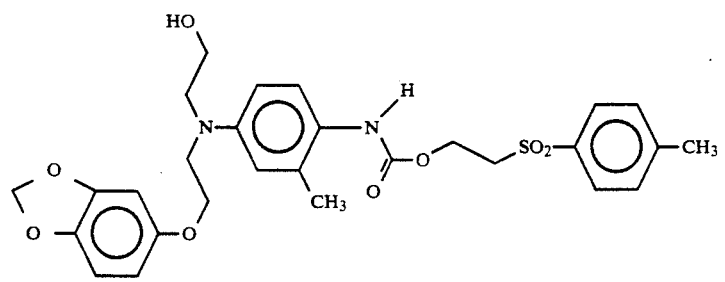
48

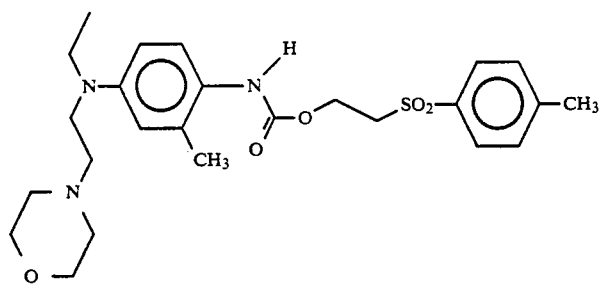
49
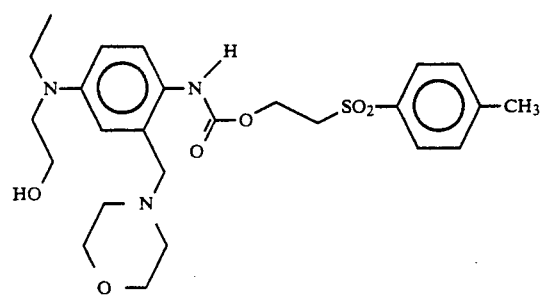
50
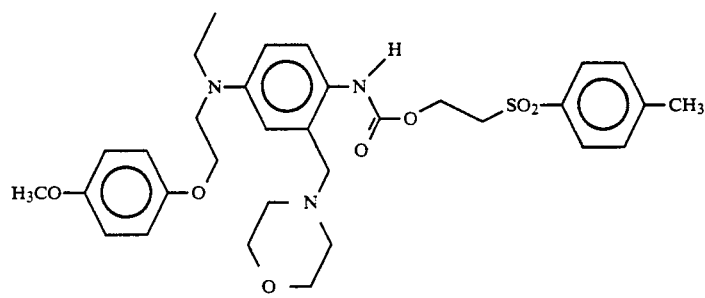
51
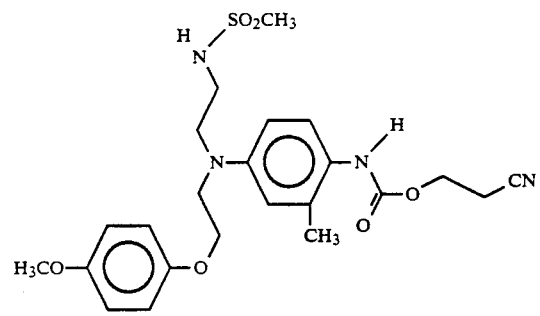
52
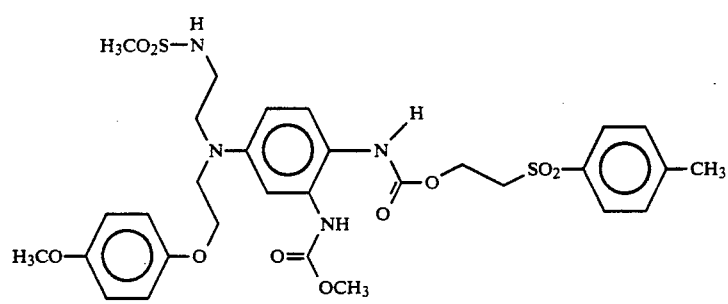
53

-continued
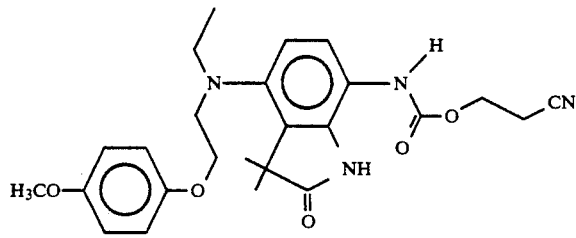
54
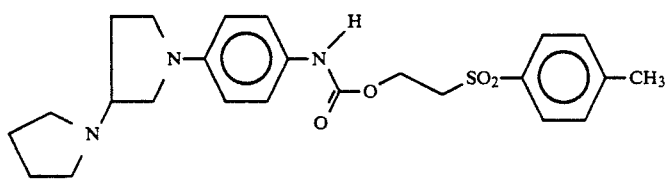
55
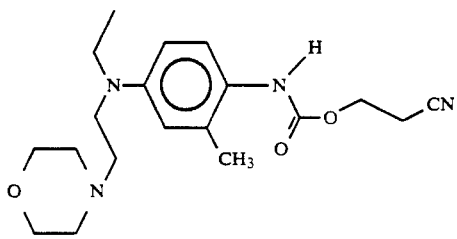
56
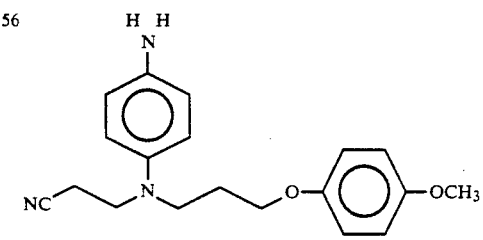
57
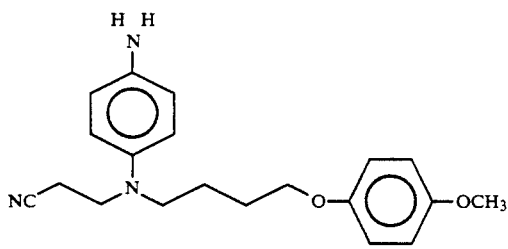
58
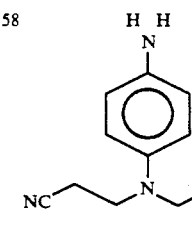
59
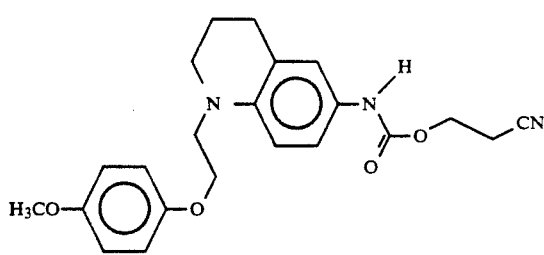
60
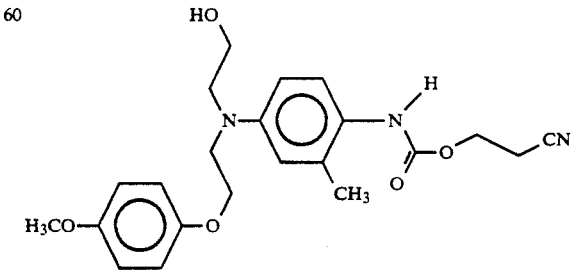
61
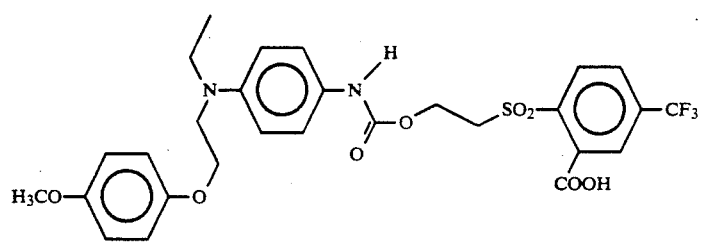
62

63 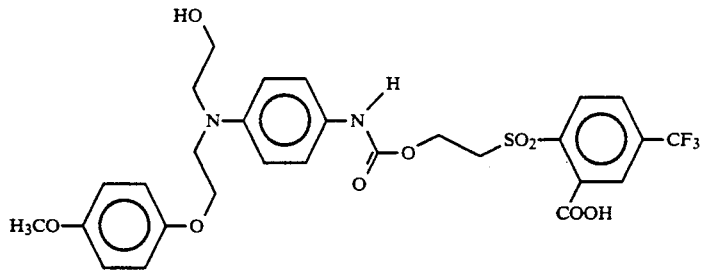
64 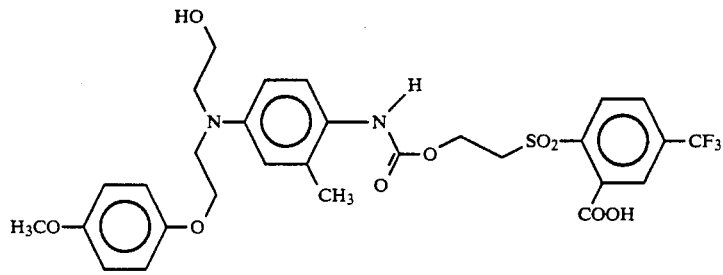
65 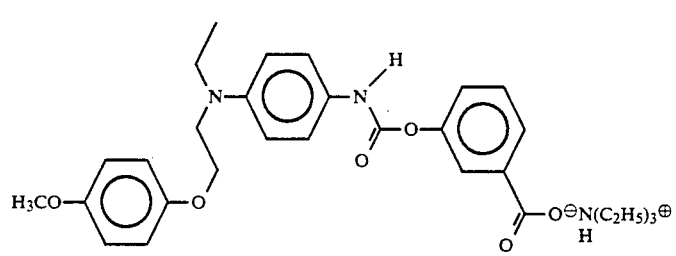
66 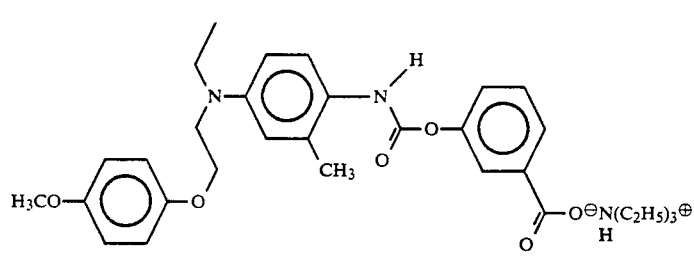
67 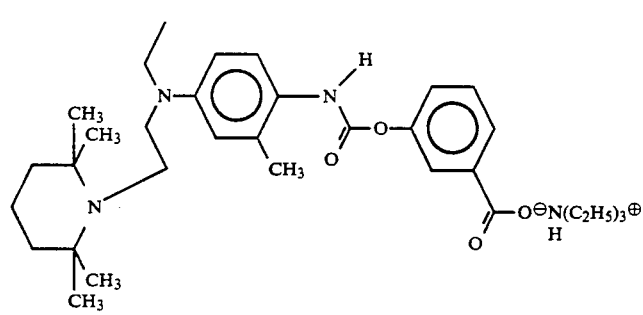
68 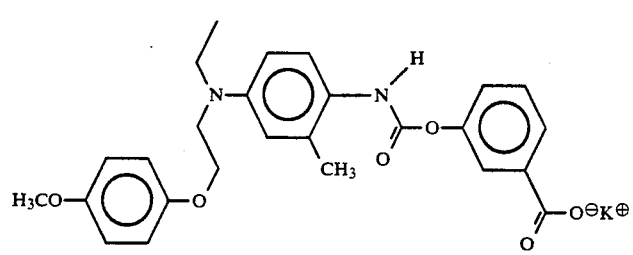

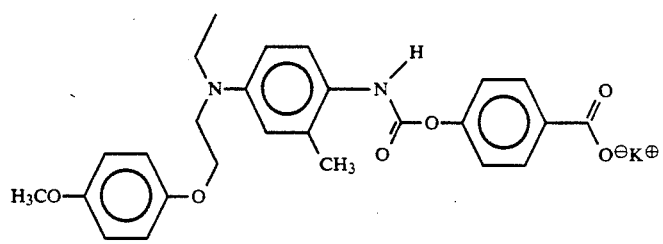
69
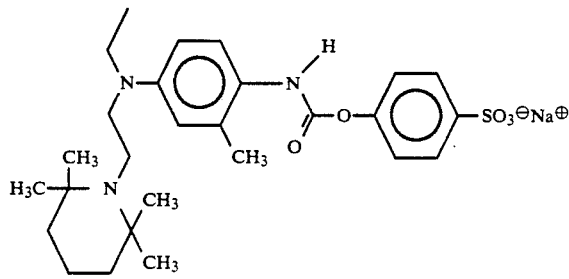
70
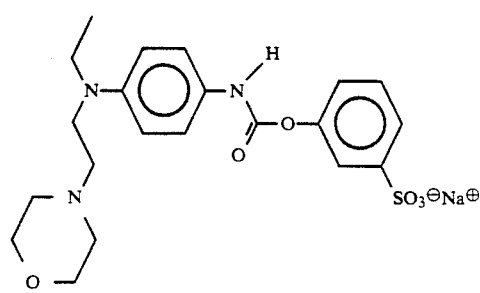
71
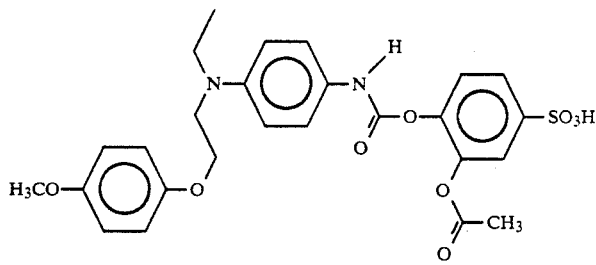
72
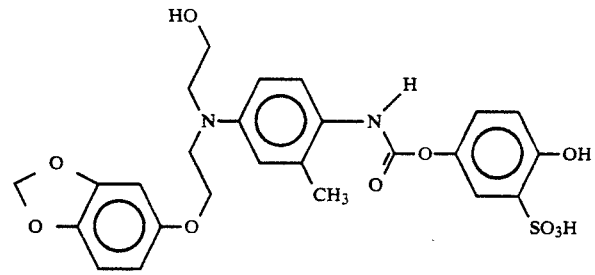
73
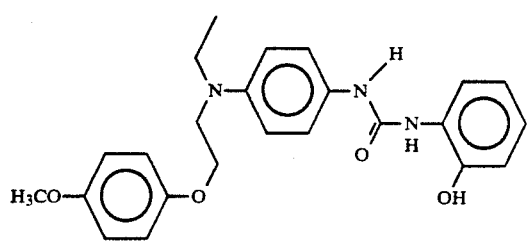
74
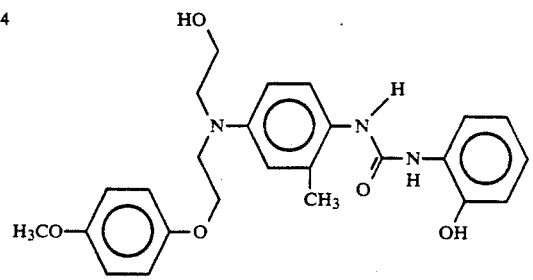
75

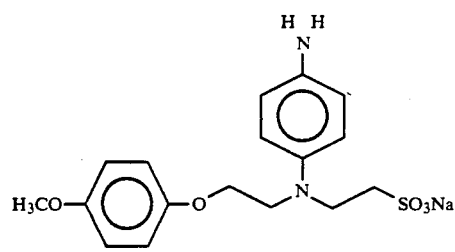
76
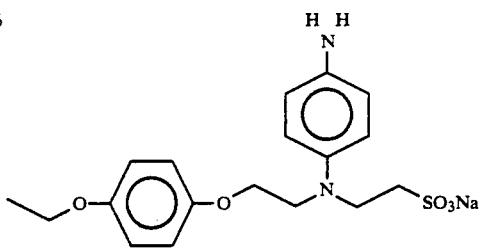
77
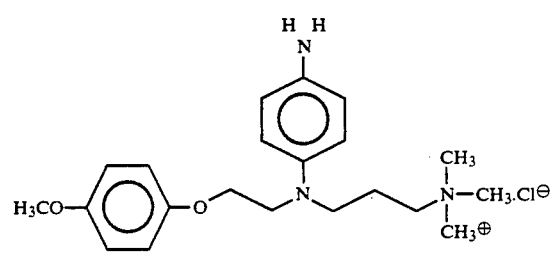
78
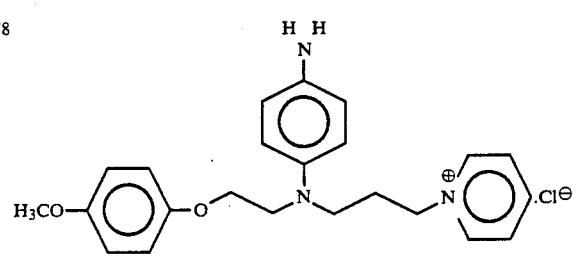
79
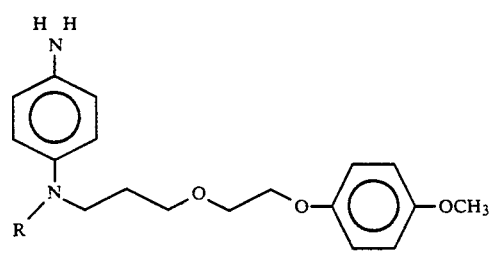
80
The description will be made on the processes for synthesizing the compounds of the present invention.
SYNTHESIS EXAMPLE-1 (SYNTHESIS OF COMPOUND 1)
The synthesis was conducted as follows:
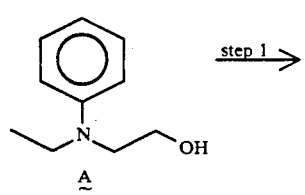
A
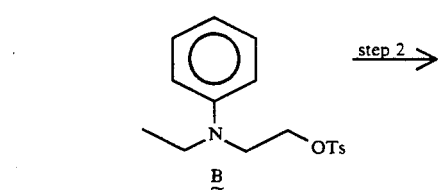
B
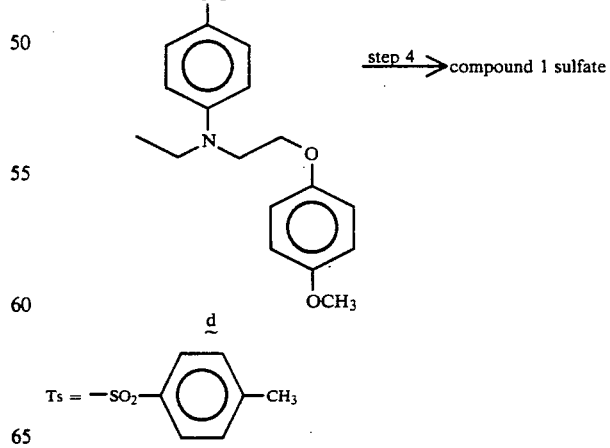
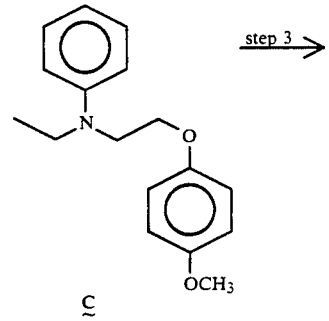
C
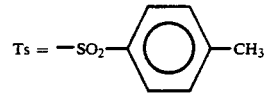

Step 1

12.7 g of tosyl chloride was added in portions to a mixture of 10 g of compound A and 50 ml of pyridine under stirring and under cooling with water. After stirring at an internal temperature of 10° C. for 1 h, 100 ml of ethyl acetate and 500 ml of water were added thereto to conduct extraction. The organic layer was washed with water twice, dried over magnesium sulfate and filtered. Compound B in the form of its solution was sent to the next step without isolation thereof.

Step 2

A mixture of 100 ml of the solution of compound B, 9.0 g of p-methoxyphenol, 12.5 g of potassium carbonate and 100 ml of N,N-dimethylacetamide was stirred at 60° C. for 4 h. The reaction liquid was cooled to 20° C. 100 ml of ethyl acetate and 500 ml of water were added thereto to conduct extraction. The organic layer was washed with water twice, dried over magnesium sulfate and filtered. The solvent was distilled under reduced pressure and then purified by silica gel column chromatography to obtain compound C in the form of a light yellow oil. Yield: 10.5 g (63.9%) (total in the two steps).

Step 3

2.8 g of sodium nitrite was added in portions to a mixture of 10 g of compound C, 50 ml of water, 8.0 ml of concentrated hydrochloric acid and 4.0 ml of tetrahydroguran under stirring and under cooling with water. They were stirred at 10° C. for 30 min and then poured into 100 ml of water. The resultant liquid was made alkaline with sodium carbonate and then extraction was conducted with ethyl acetate. The organic layer was washed with water, dried over magnesium sulfate and filtered. The solvent was distilled off under reduced pressure to obtain compound D. Yield: 10.0 g.

Step 4

Solution of 10 g of compound D in 20 ml of ethyl acetate was added to a mixture of 210 ml of isopropanol, 53 ml of water, 0.9 g of ammonium chloride and 20 g of iron powder under stirring. Then the reaction liquid was refluxed for 30 min. After cooling to lower the internal temperature of the reaction liquid to 20° C., it was filtered through Celite. A solution of 3.5 g of sulfuric acid in 50 ml of ethanol was added to the filtrate. The solvent was distilled off under reduced pressure to obtain compound 1 sulfate. Yield: 9.8 g (77%).

SYNTHESIS EXAMPLE 2 (SYNTHESIS OF COMPOUND 10)

The synthesis was conducted as follows:

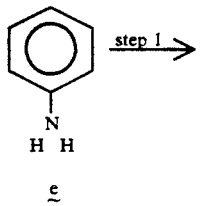

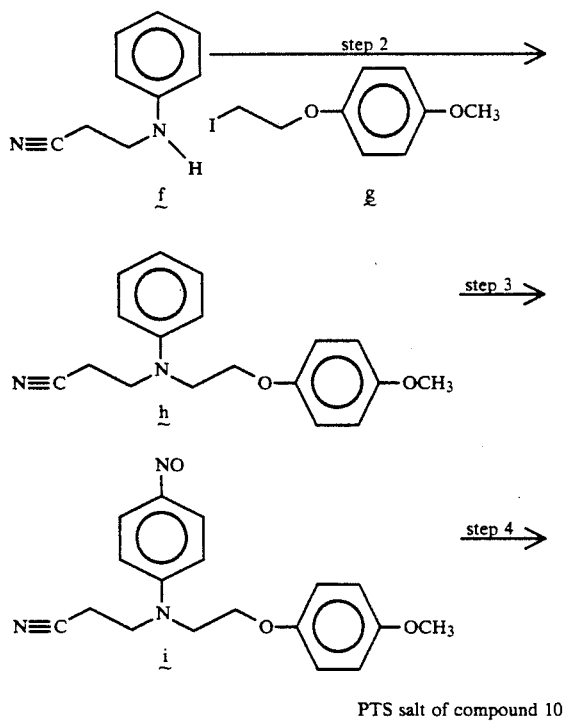

PTS salt of compound 10

Step 1

186 g of compound e, 106 g of acrylonitrile and 3.72 g of Cu(OAc)$_2$.H$_2$O were stirred together at 100° C. for 1 hr. After distillation under reduced pressure (0.8 mmHg, 131° to 135° C.), compound f was obtained. It was recrystallized from 600 ml of ethanol. Yield: 117 g (40%).

Step 2

10.5 g of compound f, 20 g of compound g, 100 ml of N,N-dimethylacetamide and 20 of potassium carbonate were stirred at 120° C. for 3 h. Then the reaction liquid was poured into 500 ml of water. After extraction with 500 ml of ethyl acetate, the organic layer was washed with water and dried. The solvent was distilled off under reduced pressure to obtain the crude product (compound h). It was purified by silica gel column chromatography to obtain compound h in the form of a light yellow oil. Yield: 13.8 g (65%).

Step 3

3.73 g of sodium nitrite was added in portions to a mixture of 12 g of compound h, 120 ml of acetic acid and 44 ml of water under stirring at 10° C. They were stirred for 1 h and the reaction liquid was poured into 500 ml of water. The mixture was made basic. After extraction with 500 ml of ethyl acetate, the organic layer was washed with water and dried. The solvent was distilled off under reduced pressure to obtain crude compound i. It was purified by silica gel column chromatography to obtain compound i in the form of a yellow oil. Yield: 7.4 g (56%).

Step 4

4.0 g of compound i, 8.0 ml of tetrahydrofuran, 80 ml of isopropanol, 20 ml of water, 0.3 g of ammonium chloride and 6.9 g of iron powder were refluxed for 30 min. The reaction liquid was cooled to 20° C. and filtered through Celite. A solution of 4.8 g of p-toluenesulfonic acid in 20 ml of ethanol was added to the filtrate. The solvent was distilled off under reduced pressure to obtain p-toluenesulfonate of compound 10 in the form of a brown powder. Yield: 6.4 g (80%). M.p. 145° to 146° C.

SYNTHESIS EXAMPLE 3 (SYNTHESIS OF COMPOUND 22)

The synthesis was conducted as follows:

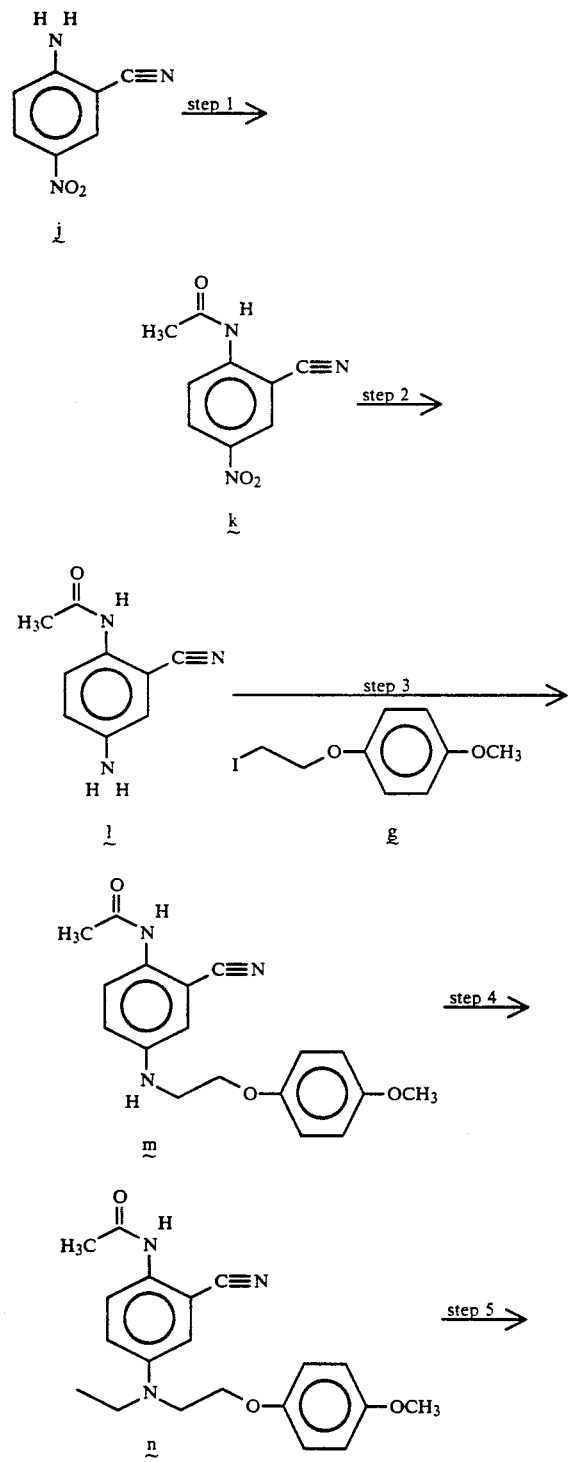

hydrochloride of compound 22

Step 1

20 g of compound j, 100 ml of acetonitrile, 14.5 g of acetyl chloride and 20 ml of N,N-dimethylacetamide were stirred at 60° C. for 4 h. The reaction liquid was poured into 500 ml of water and they were stirred for 30 min. Crystals thus formed were taken by filtration, washed with water and dried to obtain compound k. Yield: 21 g (83.3%).

Step 2

20 g of compound k, 55 g of iron powder, 2.6 g of ammonium chloride, 400 ml of isopropanol and 100 ml of water were refluxed for 30 min. The reaction liquid was cooled to 20° C. and filtered through Celite. The filtrate was distilled off under reduced pressure to obtain compound l in the form of a light brown oil. Yield: 10 g (58%).

Step 3

10 g of compound l, 11.7 g of compound g, 100 ml of N,N-dimethylacetamide and 24 g of potassium carbonate were stirred at 80° C. for 4 h. Then the reaction liquid was poured into 500 ml of water. After extraction with 500 ml of ethyl acetate, the solvent was distilled off under reduced pressure to obtain crude crystals, which were recrystallized from 50 ml of methanol to obtain compound m. Yield: 6.8 g (34%).

Step 4

3.2 g of compound m, 8.1 g of ethyl iodide, 5.5 g of potassium carbonate and 32 ml of N,N-dimethylacetamide were stirred at 100° C. for 3 h. The reaction liquid was poured into 500 ml of water. After extraction with 500 ml of ethyl acetate, the organic layer was washed with water and dried. The solvent was distilled off under reduced pressure to obtain the crude product, which was purified by silica gel column chromatography to obtain compound n. Yield: 3.0 g (82%).

Step 5

1.0 g of compound n, 6.0 ml of methanol and 3.0 ml of concentrated hydrochloric acid were stirred together at 25° C. for 3 h. Then the solvent was distilled off from the reaction liquid under reduced pressure to obtain hydrochloride of compound 22 in the form of light brown crystals. Yield: 1.1 g (96%).

The developing agents in the form of Schiff base-type precursors thereof such as compound (41) can be synthesized from an aryl aldehyde and an aromatic primary amine developing agent by a synthesis method described in J.P. KOKAI No. 56-106241.

The developing agents in the form of arylsulfonylethyl urethane-type precursors such as compound (46) can be synthesized from an arylsulfinic acid and an aromatic primary amine developing agent by a synthesis method described in J.P. KOKOKU No. 58-14671.

The developing agents in the form of cyanoethylurethane-type precursors such as compound (52) can be synthesized from aromatic primary amine developing agents by a synthesis method described in J.P. KOKOKU No. 58-14672.

The developing agents in the form of precursors such as compounds (74) and (75) can be synthesized from a developing agent, phosgene and an aniline derivative by a method described in J.P. KOKAI No. 59-53831.

Other compounds can be easily synthesized by the above-described processes.

Detailed description will be made on the use of the compounds (p-phenylenediamine derivatives) of the present invention for silver halide color photographic materials.

The compounds of the present invention can be used as the color developing agent or precursor thereof in the color development conducted in the presence of a color coupler. When they are used in the form of a developer, they are used as the active ingredient in an aqueous alkaline solution.

The amount of developing agent in the color developer is preferably $1 \times 10^{-3}$ to $1 \times 10^{-1}$ mol/l, more preferably $5 \times 10^{-3}$ to $5 \times 10^{-2}$ mol/l. In this respect, it is preferable that the color development be conducted at a temperature of 10° to 50° C., more preferably 33° to 40° C. for 20 seconds to 10 minutes.

When the developing agent is to be dissolved in the processing solution, it can be directly dissolved in the latter. In case the developing agent is difficulty soluble in the latter, it may be once dissolve in a hydrophilic solvent such as methanol or ethanol and then in the processing solution or, alternatively it may be once dissolved in an acidic aqueous solution and then in the processing solution.

The color developer usually contains a pH buffering agent such as an alkali metal carbonate, borate or phosphate; a development restrainer such as a bromide, iodide, benzimidazole, benzothiazole or mercapto compound; or a fog inhibitor. If necessary, the color developer may further contain preservatives such as hydroxylamine, diethylhydroxylamine, sulfites, hydrazines, phenylsemicarbazides, triethanolamine, catecholsulfonic acids and triethylenediamine(1,4-diazabicyclo[2,2,2]octane) compounds; organic solvents such as ethylene glycol and diethylene glycol; development accelerators such as benzyl alcohol, polyethylene glycol, quaternary ammonium salts and amines; dye-forming couplers; competing couplers; fogging agents such as sodium boron hydride; assistant developing agents such as 1-phenyl-3-pyrazolidone; thickening agents; chelating agents such as aminopolycarboxylic acids, aminopolyphosphonic acids, alkylphosphonic acids and phosphonocarboxylic acids, e.g., ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N',N'-tetramethylenephosphonic acid, ethylenediamine-di-(o-hydroxyphenylacetic acid) and salts of them.

When a reversal process is employed, usually black-and-white development is conducted and then color development is conducted. The black-and-white developer comprises one or a combination of two or more known black-and-white developing agents such as dihydroxybenzenes, e.g., hydroquinone, 3-pyrazolidones, e.g., 1-phenyl-3-pyrazolidone and aminophenols, e.g., N-methyl-p-aminophenol.

The pH of these color developers or black-and-white developers is usually 9 to 12. The amount of the developer to be replenished varies depending on the color photosensitive material to be processed. It is usually not larger than 3 l per $M^2$ of the photosensitive material. When bromide ion concentration in the replenisher is reduced, the amount of the replenisher can be reduced to 500 ml or less. When the amount of the replenisher is reduced, the evaporation of the liquid and oxidation thereof with air are preferably inhibited by reducing the contact area of the processing vessel with air. The amount of the replenisher can be reduced also by inhibiting accumulation of bromide ion in the developer.

After completion of the color development, the photographic emulsion layer is usually bleached. The bleaching process can be conducted simultaneously with the fixing process (bleach-fixing process) or separately from it. For acceleration, the bleach-fixing process may be conducted after the bleaching process. Depending on the purpose, two bleach-fixing vessels connected with each other can be employed; the fixing process can be conducted prior to the bleach-fixing process; or the bleaching process can be conducted after the bleach-fixing process. Examples of the bleaching agents include compounds of polyvalent metals such as iron (III), cobalt (III), chromium (IV) and copper (II); peracids, quinones and nitro compounds. Typical examples of the bleaching agents include ferricyanides; bichromates; organic complex salts of iron (III) or cobalt (III) such as aminopolycarboxylates, e.g., ethylenediaminetetraacetate, diethylenetriaminepentaacetate, cyclohexanediaminetetraacetate, methyliminodiacetate, 1,3-diaminopropanetetraacetate and glycol ether diaminetetraacetate and complex salts thereof with citric acid, tartaric acid, and malic acids; persulfates, bromates; permanganates; and nitrobenzenes. Among them, iron (III) complex salts of aminopolycarboxylic acids such as iron (III) salt of ethylenediaminetetraacetic acid and persulfates are preferred from the viewpoints of the rapid process and prevention of environmental pollution. The iron (III) complex salts of aminopolycarboxylic acids are particularly effective in both bleaching solution and bleach-fixing solution. The pH of the bleaching solution or bleach-fixing solution containing such an iron (III) complex salt of aminopolycarboxylic acid is usually 5.5 to 8. For acceleration of the process, a lower pH can also be employed.

The bleaching solution, bleach-fixing solution, prebleaching bath and prebleach-fixing bath may contain a bleaching accelerator, if necessary. Examples of the bleaching accelerators include compounds having a mercapto group or disulfide bond described in U.S. Pat. No. 3,893,858, West German Patent No. 1,290,812, J.P. KOKAI No. 53-95,630 and Research Disclosure No. 17,129 (July, 1978); thiazolidine derivatives described in J.P. KOKAI No. 50-140,129; thiourea derivatives described in U.S. Pat. No. 3,706,561; iodides described in J.P. KOKAI No. 58-16,235; polyoxyethylene compounds described in West German Patent No. 2,748,430; polyamine compounds described in J.P. KOKOKU No. 48-8836; and bromide ions. Among them, the compounds having a bercapto group or disulfido bond are preferred, since they have a remarkable acceleration effect. Compounds described in U.S. Pat. No. 3,893,858, West German Patent No. 1,290,812 and J.P. KOKAI No. 53-95,630 are particularly preferred. Further compounds described in U.S. Pat. No. 4,552,834 are also preferred. These bleach-accelerators may be added to the photosensitive material. When a color photosensitive material for photography is to be bleach-fixed, these bleaching accelerators are particularly effective.

The fixing agents include, for example, thiosulfates, thiocyanates, thioether compounds, thioureas and a large amount of iodides. Among them, the thiosulfates are commonly used and ammonium thiosulfate is most widely usable. Preferred examples of the preservatives for the bleach-fixing solutions include sulfites, hydrogensulfites, sulfinates and carbonylhydrogensulfite adducts.

The color photosensitive silver halide material used in the present invention is usually subjected to washing with water and/or stabilization step after desilverization. The amount of water used in the washing step varies in a wide range depending on the properties of the photosensitive material (such as couplers used), temperature of water used for washing, number of the tanks used for washing with water (number of stages), replenishing method such as counter flow or down-flow system and various other conditions. Among them, the relationship between the number of the tanks for washing with water and the amount of water can be determined by a method described in "Journal of the Society of Motion Picture and Television Engineers", Vol. 64, pages 248 to 253 (May, 1955).

Although the amount of water necessitated for washing can be remarkably reduced by the multi-stage counter flow system described in the above-described journal, another problem is posed in this method that bacteria propagate themselves while the photosensitive material is kept for a longer time in the tanks and, as a result, a suspended matter thus formed is fixed on the sensitive material. For solving this problem in the processing of the color photosensitive material of the present invention, a quite effective method for reducing in amount of calcium ion and magnesium ion described in J.P. KOKAI No. 62-288838 can be employed. Further this problem can be solved also by using isothiazolone compounds described in J.P. KOKAI No. 57-8,542, thiabendazoles, chlorine-containing germicides such as chlorinate sodium isocyanurates, benzotriazoles and germicides described in Hiroshi Horiguchi "Bokin Bobai-zai no Kagaku", "Biseibutsu no mekkin, Sakkin, Bobai Gijutsu" edited by Eisei Gijutsukai and "Bokin-bobai-zai Jiten" edited by Nippon Bokinbobai Gakkai.

The pH of washing water used in combination with the processing liquid containing the developing agent of the present invention is 4 to 9, preferably 5 to 8. The temperature of water to be used for washing and the washing times which vary depending on the properties and use of the photosensitive material are usually 15° to 45° C. and 20 sec to 10 min, respectively, and preferably 25° to 40° C. and 30 sec to 5 min. The photosensitive material of the present invention can be process directly with a stabilizing solution in place of washing with water. The stabilization can be conducted by any of known processes described in J.P. KOKAI Nos. 57-8,543, 58-14,834 and 60-220,345.

The washing process with water may be followed by a stabilization process. In the stabilization, a stabilizing bath containing formalin and a surfactant which is usually used as the final bath for a color photographing photosensitive material can be used. The stabilizing bath may also contain chelating agents and mold-proofing agents.

An overflow obtained by washing with water or replenishing the stabilizing solution can be used again in another step such as desilverization step.

The color photosensitive silver halide material used in the present invention may contain a color developing agent for the purpose of simplifying and accelerating the process. The color developing agents are preferably used in the form of precursors thereof in such a case.

The color photosensitive material comprising a silver halide of the present invention may contain a 1-phenyl-3-pyrazolidone compound, if necessary, for the purpose of accelerating the color development. Typical examples of the compounds are described in J.P. KOKAI Nos. 56-64,339, 57-144,547 and 58-115,438.

The temperature of the processing solutions used in the present invention are controlled at 10° to 50° C. The standard temperature is 33° to 68° C., but a higher temperature can be employed to accelerate the process and thereby to reduce the process time or, on the contrary, a lower temperature can also be employed to improve the quality of the image and stability of the processing liquid. To save silver in the photosensitive material, intensification with cobalt or hydrogen peroxide as described in West German Patent No. 2,226,770 and U.S. Pat. No. 3,674,499 can be employed.

The developer containing the developing agent of the present invention can be employed in any processing step of wet method such as methods for processing a color paper, color reversal paper, color positive film, color negative film, color reversal film and direct positive color photosensitive material. It is particularly preferably used in processing the color paper, color negative film or color reversal film.

The silver halide emulsion for forming the photosensitive material used in the present invention may comprise any halogen composition such as silver bromoiodide, silver bromide, silver chlorobromide or silver chloride.

In the rapid process or when the amount of the replenisher is to be reduced, a silver chlorobromide emulsion or silver chloride emulsion containing at least 60 molar % of silver chloride is preferably used. The emulsion containing 80 to 100 molar % of silver chloride is particularly preferred. When a high sensitivity is necessitated or when the fogging should be strictly inhibited in the course of production, shortage and/or process, a silver chlorobromide emulsion or silver bromide emulsion containing at least 50 molar % of silver promide is preferably used and that containing at least 70 molar % thereof is more preferably used. Although the rapid process becomes difficult when silver bromide content is increased to 90 molar % or above, the development can be accelerated to some extent irrespective of the silver bromide content by using a development accelerator such as a silver halide solution, fogging agent or developing agent in the process. This technique is sometimes preferred. In both cases, use of silver iodide in a large amount is undesirable. The amount of silver iodide should be not more than 3 molar %. Such a silver halide emulsion is preferably used mainly for photosensitive materials for printing such as color papers.

The silver halides to be contained in the color photographic photosensitive materials for taking a picture (negative films and reversal films) are preferably silver bromoiodide and silver chlorobromoiodide. Silver iodide content is preferably 3 to 15 molar %.

The above-described silver halide grains may comprise a core and a surface layer (core/shell grains) or a homogeneous phase or it may have a polyphase structure (conjugated structure) or, alternatively, the grains may comprise a combination of them.

The average size of these silver halide grains (in terms of grain diameter when the grains are spherical or nearly spherical, or edge length when the grains are cubic, and they are given in terms of average based on the projection area) (the average size of tabular grains is given in terms of that of the spherical grains) used in the present invention is preferably 0.1 to 2 μm, particularly preferably 0.15 to 1.5 μm. The grain size distribution is either narrow or wide. The coefficient of variation calculated by dividing the standard deviation in the grain size distribution curve of the silver halide emulsion by the average grain size is preferably not higher than 20%, and particularly preferably not higher than 15% (so-called monodisperse silver halide emulsion) in the present invention. To satisfy an intended gradation, a layer may comprises a mixture of two or more monodisperse silver halide emulsions (preferably having the above-described coefficient of variation) having different grain sizes or the emulsions may be used for forming respective laminated layers having substantially the same color sensitivity. Further a combination of two or more polydisperse silver halide emulsions or a combination of a monodisperse emulsion with a polydisperse emulsion can be used in the form of a mixture or by forming a laminated layers thereof.

The silver halide grain used in the present invention may be in a regular crystal form such as cubic, octahedral, rhombo-dodecahedral or tetradecahedral form or a mixture of them; or an irregular crystal form such as spherical form; or a complex crystal form thereof. They may also be tabular grains. Particularly an emulsion wherein at least 50% of the total projection area of the grains comprise tabular grains having a length/thickness ratio of at least 5, particularly at least 8 is usable. The emulsion may comprise a mixture of grains having various crystal forms. The emulsion may be of a surfacelatent-image type for forming a latent image mainly on the surfaces thereof or of an internal latent-image type for forming a latent image in the grains.

The photographic emulsions for photosensitive materials for which the developer containing the developing agent of the present invention is used can be product by a method disclosed in Research Disclosure (RD), Vol. 176, Item No. 17643, (Paragraphs I, II and III) (December, 1978).

Such a silver halide emulsion is usually physically and chemically ripened and spectrally sensitized. The additives to be used in these steps are shown in Research Disclosure, Vol. 176, No. 17643 (December, 1978) and Vol, 187, No. 18716 (November, 1979). The portions in which the additives are mentioned in these two Research Disclosures are summarized in the following table.

Known photographic additives for the photosensitive materials for which the developer containing the developing agent of the present invention can be used are also mentioned in the two Research Disclosures and the corresponding portions are also shown in the following table.

|   | ADDITIVE | RD 17643 | RD 18716 |
|---|---|---|---|
| 1 | Chemical sensitizer | p. 23 | right column, p. 648 |
| 2 | Sensitivity improver | p. 23 | right column, p. 648 |
| 3 | Spectral sensitizer | pp. 23 to 24 | right column, p. 648 to right column, p. 649 |
| 4 | Supersensitizer | pp. 23 to 24 | |
| 5 | Brightening agent | p. 24 | |
| 6 | Antifoggant and stabilizer | pp. 24 to 25 | right column, p. 649 |
| 7 | Coupler | p. 25 | right column, p. 649 |
| 8 | Organic solvent | p. 25 | right column, p. 649 |
| 9 | Light absorber and filter dye | pp. 25 to 26 | right column, p. 649 to left column, p. 650 |
| 10 | U.V. absorber | pp. 25 to 26 | right column, p. 649 to left column, p. 650 |
| 11 | Antistaining agent | right column, p. 25 | left and right columns, p. 650 |
| 12 | Dye image stabilizer | p. 25 | left and right columns, p. 650 |
| 13 | Hardener | p. 26 | left column, p. 651 |
| 14 | Binder | p. 26 | left column, p. 651 |
| 15 | Plasticizer and lubricant | p. 27 | right column, p. 650 |
| 16 | Coating aid and surfactant | pp. 26–27 | right column, p. 650 |
| 17 | Antistatic agent | p. 27 | right column, p. 650 |

Various color couplers can be used for the photosensitive material used in the present invention. The color couplers herein indicate compounds capable of coupling with an oxidation product of an aromatic primary amine developing agent to form a dye. Typical examples of the useful color couplers include naphthol or phenol compounds, pyrazolone or pyrazoloazole compounds and open chain or heterocyclic ketomethylene compounds. Further, imidazopyrazole compounds, pyrazoloquinazolone compounds and imidazole compounds recently proposed can also be used. Examples of these cyan, magenta and yellow couplers usable in the present invention are described in patents cited in Research Disclosure (RD) 17643 (December, 1978) VII-D and 18717 (November, 1979).

The color couplers contained in the photosensitive material preferably has a ballast group or they are made nondiffusible by polymerization. When a divalent color couplers wherein the active coupling portions are substituted with a coupling-off group are used, the amount of silver used for coating is smaller than that required when a tetravalent color coupler having hydrogen atoms at the active coupling portions is used. Couplers capable of forming a colored compound having suitable diffusing properties, colorless compound forming couplers, DIR couplers capable of releasing a development inhibitor by coupling reaction or couplers capable of releasing a development accelerator are also usable.

Typical examples of the yellow couplers usable in the present invention include oil protection type acylacetamide couplers such as those described in U.S. Pat. Nos. 2,407,210, 2,875,057 and 3,265,506. Divalent yellow couplers are preferably used in the present invention. Typical examples of them include yellow couplers of oxygen-linked coupling-off type such as those disclosed in U.S. Pat. Nos. 3,408,194, 3,447,928, 3,933,501 and 4,022,620, and yellow couplers of nitrogen-liked coupling-off type such as those disclosed in J.P. KOKOKU No. 55-10739, U.S. Pat. Nos. 4,401,752, and 4,326,024, RD 18053 (April, 1979), British Patent No. 1,425,020, and West German Public Disclosure Nos. 2,219,917, 2,261,361, 2,329,587 and 2,433,812. α-Pivaloylacetanilide couplers provide excellent fastness, particularly light fastness, of the developed dye and, on the other hand, α-benzoylacetaniline couplers provide a high developed color density.

The magenta couplers usable in the present invention include oil-protection type indazolone or cyanoacetyl couplers, preferably 5-pyrazolone and pyrazoloazole couplers such as pyrazolotriazoles. Among the 5-pyrazolone couplers, those having an arylamino group or an acylamino group at 3-position are preferred in view of the hue of the developed color and the developed color density. Typical examples of them are mentioned in U.S. Pat. Nos. 2,311,082, 2,343,703, 2,600,788, 2,908,573, 3,062,653, 3,152,896 and 3,936,015. Nitrogen-linked coupling-off groups described in U.S. Pat. No. 4,310,619, and arylthio groups mentioned in the U.S. Pat. No. 4,351,897 are particularly preferred as the releasing group of the 2-equivalent 5-pyrazolone couplers. 5-Pyrazolone couplers having a ballast group mentioned in European Patent No. 73,636 provide a high developed color density.

Examples of the pyrazoloazole couplers include pyrazolobenzimidazoles described in U.S. Pat. No. 3,369,879, preferably pyrazolo [5,1-c][1,2,4]triazoles described in U.S. Pat. No. 3,725,067, pyurazolotetrazoles described in Research Disclosure 24220 (June, 1984) and pyrazolopyrazoles described in Research Disclosure 24230 (June, 1984). Imidazo[1,2-b]pyrazoles described in European Patent No. 119,741 are preferred because of low yellow subabsorption and light fastness of the developed dye, and pyrazolo[1,5-b]1,2,4]triazole described in European Patent No. 119,860 is particularly preferred.

The cyan couplers usable in the present invention include oil-protection-type naphthol and phenol couplers. Examples of them include naphthol couplers described in U.S. Pat. No. 2,474,293, preferably oxygen-linked coupling-off type 2-equivalent naphthol couplers described in U.S. Pat. Nos. 4,052,212, 4,146,396, 4,228,233 and 4,296,200. Examples of the phenol couplers are described in U.S. Pat. Nos. 2,369,929, 2,801,171, 2,772,162 and 2,895,826. The cyan couplers stable to moisture and temperature are preferably used in the present invention. Typical examples of them include phenolic cyan couplers having an alkyl group higher than ethyl group inclusive at m-position of the phenol nucleus as described in U.S. Pat. No. 3,772,002; 2,5-diacylamino-substituted phenol couplers as described in U.S. Pat. Nos. 2,772,162, 3,758,308, 4,126,396, 4,334,011 and 4,327,173, West German Patent Public Disclosure No. 3,329,729 and J.P. KOKAI No. 59-166956; and phenol couplers having a phenylureido group at 2-position and an acylamino group at 5-position as described in U.S. Pat. Nos. 3,446,622, 4,333,999, 4,451,559 and 4,427,767.

The graininess can be improved by using an additional coupler to provide colored dye which is suitably diffusible. Examples of such couplers include magenta couplers described in U.S. Pat. No. 4,366,237 and British Patent No. 2,125,570; and yellow, magenta and cyan couplers described in European Patent No. 96,570 and West German Public Disclosure No. 3,234,533.

The dye-forming couplers and the above-mentioned, special couplers may form a dimer or a higher polymer. Typical examples of the polymerized dye-forming couplers are described in U.S. Pat. Nos. 3,451,820 and 4,080,211. Examples of the polymerized magenta couplers are described in British Patent No. 2,102,173 and U.S. Pat. No. 4,367,282.

Two or more kinds of the couplers usable in the present invention can be contained in the same photosensitive layer or the same compound can be contained in two or more layers in order to obtain the necessary properties of the photosensitive material.

The couplers usable in the present invention can be introduced into the photosensitive material by various known dispersion methods. Examples of high-boiling organic solvents usable in an oil-in-water dispersion method are described in, for example, U.S. Pat. No. 2,322,027. The steps and effects of latex dispersion method (a polymer dispersion method) and examples of the latices usable for the impregnation are described in U.S. Pat. No. 4,199,363, and West German Patent Application (OLS) Nos. 2,541,274 and 2,541,230. A dispersion method wherein an organic solvent-soluble polymer is used is described in PCT Application No. JP 87/00492.

Examples of the organic solvents usable in the oil-in-water dispersion method include alkyl phthalates (such as dibutyl phthalate and dioctyl phthalate), phosphoric esters (such as diphenyl phosphate, triphenyl phosphate, triciesyl phosphate and dioctylbutyl phosphate), citric esters (such as tributyl acetylcitrate), benzoic esters (such as octyl benzoate), alkylamides (such as diethyllaurylamide), fatty acid esters (such as dibutoxyethyl succinate and diethyl azelate), trimesic esters (such as tributyl trimesate); those having a boiling point of about 30° to 150° C. such as lower alkyl acetates (e.g. ethyl acetate and butyl acetate), ethyl propionate, sec-butyl alcohol, methyl isobutyl ketone, $\beta$-ethoxyethyl acetate and methyl cellosolve acetate.

The standard amount of the color coupler ranges form 0.001 to I mol per mol of the photosensitive silver halide. Preferably the yellow coupler is used in an amount of 0.01 to 0.5 mol, magenta coupler is used in an amount of 0.003 to 0.3 mol and cyan coupler is used in an amount of 0.002 to 0.3 mol.

The photographic photosensitive material used in the present invention is applied to an ordinary flexible support such as a pinistic film (e.g. cellulose nitrate, cellulose acetate or polyethylene terephthalate film) or paper; or a rigid support such as a glass support. The details of the supports and coating methods are described in Research Disclosure No. 176, Item 17643XV (p. 27) and XVII (p. 28) (December, 1978).

When the present invention is employed in processing a color paper, a reflecting support is preferably used. The term "reflecting support" herein indicates a support having an improved reflectively so as to form a clear dye image in the silver halide emulsion layer. The reflecting supports are produced by coating the support with a dispersion of a light-reflecting substance such as titanium oxide, zinc oxide, calcium carbonate or calcium sulfate in a hydrophobic resin. Further supports made of a hydrophobic resin containing such a light-reflecting substance dispersed therein are also usable.

The developing agent of the present invention or precursor thereof can be incorporated into the photosensitive material so that a color image will be formed by color development process with an alkali solution. This will be illustrated below.

The precursor of the developing agent of the present invention can be contained in any layer containing a hydrophilic colloid in the color photosensitive material. The layer is, for example, a surface-protecting layer, photosensitive layer (such as a silver halide emulsion layer), a layer between the surface-protecting layer and the photosensitive layer, or an image-receiving layer for color diffusion transfer process (containing also an oxidizing agent). Preferably, the compound of the present invention is contained in two hydrophilic colloid layers between which the photosensitive material is interposed.

The precursor of the developing agent of the present invention can be incorporated into the aqueous hydrophilic colloid solution as follows: when the precursor of the developing agent of the present invention is soluble in water, an aqueous solution thereof can be added to an aqueous solution of a hydrophilic colloid. When the precursor of the developing agent is difficultly soluble (sparingly soluble) in water, a latex dispersion process of oil-in-water emulsification dispersion process is effective. These processes are well known. The latex dispersion process is described in, for example, J.P. KOKAI Nos. 49-74538 and 51-59943. The oil-in-water emulsification dispersion process is ordinarily employed for dispersing a hydrophobic additive such as a coupler. Therefore, when the emulsification dispersion process is employed, a coupler solvent which will be described below can be used as an oil for dissolving the compound of the present invention.

For dispersing the oil phase containing the compound of the present invention dissolved therein an aqueous phase, a surfactant is usually used. The surfactants include, for example, anionic surfactants having an acid group such as carboxylic acid, sulfonic acid or phosphoric acid group or sulfuric ester or phosphoric ester group; and nonionic, cationic or amphoteric surfactants. Examples of them are well known in the art.

The hydrophilic colloids usable herein include, for example, gelatin and those known as photographic binders. They can be used in combination with a latex. Examples of them include compounds described in U.S. Pat. No. 3,518,088 and Research Disclosure No. 14,814,850 (August, 1976).

Known photographic antioxidants or stabilizers can be incorporated into the coating solution containing the compound of the present invention. They include, for example, hydroquinone derivatives, reductones such as ascorbic acid, hydroxylamines, sulfonyl compounds and active methylene compounds.

The compound of the present invention is used in an amount of 0.1 to 10 mol, preferably 0.25 to 5 mol, per mol of total silver in the photosensitive material per a unit area.

The development process for the color photosensitive material with the precursor of the developing agent of the present invention is the same as an ordinary color development process except that an alkali activator bath is used in place of the color development bath. Therefore, after the color development step with the activator bath, the ordinary steps can be employed. Namely, the color development step is followed by a desilverization step which essentially comprises bleaching and fixing steps. These steps can be conducted in this order or at the same time.

In the practical development process, additional steps are employed in order to maintain the photographic and physical qualities of the image or to improve the storability of the image, in addition to the two fundamental steps, i.e. color development step and desilverization step. For example, a hardening bath for preventing excess softening of the photosensitive film during the process, terminating bath for effectively terminating the development reaction, image-stabilization bath for stabilizing the image or film-removing bath for removing a packing layer from the support can be used.

The activator bath used for processing the color photosensitive material containing the precursor of the developing agent of the present invention essentially corresponds to an ordinary developer but free from any color developing agent. Therefore, known additives for color developers can be used as they are. Examples of them are described in, for example, J.P. KOKAI Nos. 52-27638 and 50-145125. However, no preservative is necessitated. In color diffusion transfer processes, a black-and-white developing agent such as phenidone is preferably used.

The pH of the activator bath is preferably relatively higher than that of the ordinary developer so that the precursor will be rapidly decomposed with an alkali. In particular, pH in the range of about 10 to 14 is preferred. The temperature of the activator bath is 20° to 70° C., preferably 30° to 60° C.

Ordinary nondiffusible couplers which can be incorporated into the color photosensitive material containing the precursor of the developing agent of the present invention include ordinary couplers. Development inhibitor-releasing couplers (so-called DIR couplers) and other development inhibitor-releasing compounds can be used in the color reaction. Examples of them are described in U.S. Pat. Nos. 3,148,062, 3,227,554, 3,253,924, 3,617,291, 3,622,328 and 3,705,201, British Patent No. 1,201,110, and U.S. Pat. Nos. 3,297,445, 3,379,529 and 3,639,417.

Two or more of these couplers can be incorporated into one layer or one and the same compound can be incorpated into two or more layers to as to satisfy the requirements of the photosensitive material.

The coupler can be dispersed in a hydrophilic colloid by latex dispersion method or oil-in-water emulsification dispersion method.

The coupler is soluble in a solvent for the coupler (preferably an oil having a suitable polarity) but preferably insoluble in water. Typical examples of the useful solvents include tri-o-cresyl phosphate, trihexyl phosphate, dioctylbutyl phosphate, dibutyl phthalate, dethyllaurylamide, 2,4-diallylphenol and compounds described as 'Improved dye image-stabilizing solvent for photography' in Product Licensing Index, Vol. 83, pp. 26 to 29 (March, 1971).

A silver halide emulsion used for forming the photosensitive material for which the precursor of the developing agent of the present invention is used can be produced by a known process. Namely, starting materials such as silver halides and binder for the emulsion, photographic additives such as chemical sensitizers and spectral sensitizers, used for the production of the emulsion, processes for applying the emulsion to form a coating and supports are not particularly limited and ordinary ones can be employed. Examples of them are described in, for example, J.P. KOKAI Nos. 52-27638 and 50-145125.

In addition, the silver halide emulsion used in the present invention may be either a surface-latent image type emulsion or internal latent image type emulsion. When the silver halide emulsion used in the present invention is a direct positive emulsion, it may be previously fogged prior to the image-forming exposure or it may be fogged after the image-forming exposure.

The color photosensitive material used in the present invention can be used for the production of color negative films, color positive films, color papers and color diffusion transfer film units.

The developing agent for color development or the precursor thereof the present invention can be incorporated into the photosensitive material so that a color image can be formed by thermal developing step.

The compounds of the present invention to be contained in the color photosensitive material for the thermal development can be used either singly or in combination of two or more of them. The amount of the compound used varies depending on the kind of the silver salt used as the oxidizing agent (such as an organic silver salt), kind of the photosensitive silver halide and other additives used. It is usually in the range of 0.05 to 10 mol, preferably 0.1 to 3 mol, per mol of the silver salt used as the oxidizing agent. The method of the incorporation is not limited. For example, when a hydrophilic binder is used, it is dissolved in a hydrophilic solvent and the solution is incorporated thereinto or, alternatively, it is dissolved in a solvent immiscible with water and the solution is dispersed therein by a method known in the art. When a hydrophobic binder is used, it can be dissolved in a solvent miscible therewith which does not precipitate the binder in the binder solution and the solution is incorporated thereinto. When it is soluble only in a solvent immiscible with the solvent in the binder solution, it can be dissolved therein and the solution is dispersed therein. In either case, the compound in the form of the solid can be directly dispersed therein.

The dye donators used when the developing agent of the present invention is applied to the color photosensitive material for thermal development include, for example, those described in J.P. KOKAI No. 62-44737, non-diffusible dye-forming couplers described in Japanese Patent Application Nos. 60-271117 and 61-11563, leuco dyes described in U.S. Pat. No. 475,441, and azo dyes used for thermal development/dye bleaching method described in U.S. Pat. No. 4,235,957. More preferred are diffusible dye-donators capable of forming or releasing diffusible dyes, particularly compounds capable of forming diffusible dyes by the coupling reaction. The diffusible dye-donators and negative type dye-donators used and the method of use are described on pages 4 and 5 of J.P. KOKAI No. 62-44737.

The photosensitive silver halides used for producing the color photosensitive materials for the thermal development, and chemical sensitization method and spectral sensitization method thereof are described on pages 5 to 7 of J.P. KOKAI No. 63-301037. Organic silver salts used, if necessary, for improving the sensitivity and the amount thereof are described on pages 7 and 8 of J.P. KOKAI No. 63-301037.

The compounds of the present invention can be used in combination with developing agents usually used in the field of the photosensitive materials for the thermal development. Examples of these developing agents are described on page 8 of J.P. KOKAI No. 63-301037.

The binders and supports are those usually used in the art. Examples of them are described on pages 8 and 9 of J.P. KOKAI No. 63-301037.

It is preferred to add a thermal solvent to the photosensitive material for thermal development and/or image-receiving member used in the present invention particularly when the photosensitive material is of the transfer type and the image-receiving member is used. The thermal solvent is a compound capable of accelerating the thermal development and/or thermal transfer. These compounds are described in, for example, U.S. Pat. Nos. 3,347,675 and 3,667,959, RD (Research Disclosure) No. 17643 (XII) and J.P. KOKAI No. 63-301037.

When the present invention is employed in the photosensitive material for thermal development of transfer system, an image-receiving member is provided as described above. The effective image-receiving layer of the image-receiving member has a function of receiving dyes released from or formed in the photosensitive layer by the thermal development. The layer comprises, for example, a polymer containing a tertiary amine or quaternary ammonium salt described in U.S. Pat. No. 3,709,690. A typical image-receiving layer for the diffusion transfer is produced by mixing a polymer containing an ammonium salt or tertiary amine with gelatin, polyvinyl alcohol or the like and applying the mixture to a support. Another effective dye-receiving substance comprises a heat-resistance organic polymer having a glass transition temperature of 40° to 250° C. as described in J.P. KOKAI No. 57-207250.

These polymers can be used as a receiving layer to be formed on the support or they per se can be used as the support.

The photosensitive material for the thermal development used in the present invention can be a so-called monotone photosensitive material comprising a photosensitive layer and a receiving layer formed on one support as described in RD (Research Disclosure) No. 15108 and J.P. KOKAI Nos. 57-198458, 57-207250 and 61-80148.

EXAMPLE 1

A multi-layered color photographic paper having the following layer construction was prepared by subjecting the surface of a paper support the both surfaces of which had been laminated with polyethylene to corona discharge treatment, forming a gelatin-primer layer containing sodium dodecylbenzenesulfonate and forming various photographic layers thereon. The coating liquids were prepared as follows: Preparation of coating solution for forming the first layer:

27.2 ml of ethyl acetate, 4.1 g of a solvent (Solv-3) and 4.1 g of solvent (Solv-7) were added to a mixture of 19.1 g of yellow coupler (ExY), 4.4 g of a color image stabilizer (Cpd-1) and 0.7 g of another color image stabilizer (Cpd-7) to prepare a solution, which was emulsification-dispersed in 185 ml of 10 % aqueous gelatin solution containing 8 ml of 10% sodium dodecylbenzenesulfonate to obtain emulsion/dispersion A. On the other hand, a silver chlorobromide emulsion A was prepared. This emulsion comprised a mixture of a large size emulsion A of cubic grains having an average grain size of 0.88 g $\mu$m and a small size emulsion A of those of 0.70 $\mu$m in a molar ratio of 3:7 (in terms of silver); (coefficient of variation of grain size distribution: 0.08 and 0.10, respectively; and each containing 0.3 molar % of silver bromide in a part of the grain surface layer). The large size emulsion A contained each $2.0 \times 10^{-4}$ mol, per mol of silver, of blue-sensitive sensitizing dyes A and B and the small size emulsion A contained each $2.5 \times 10^{-4}$ mol of them. The emulsion A was chemically aged by addition of a sulfur sensitizer and a gold sensitizer. This silver chlorobromide emulsion A was mixed with the above-described emulsion dispersion A prepared as described above to form a solution. The solution for forming the first layer and having a composition which will be given below was prepared.

Coating solutions for forming the second layer through the seventh layer were prepared in the same manner as that for forming the first coating solution. Sodium salt of 1-hydroxy-3,5-dichloro-striazine was used as the gelatin hardener in each layer.

Cpd-10 and Cpd-11 in total amounts of 25.0 mg/m$^2$ and 50.0 mg/m$^2$, respectively, were incorporated into the respective layers.

The following spectral sensitizing dyes were incorporated into the silver chlorobromide emulsions used for forming the respective photosensitive emulsion layers.
Sensitizing dye A for blue-sensitive emulsion layer:

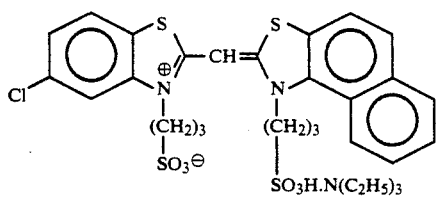

Sensitizing dye B for blue-sensitive emulsion layer

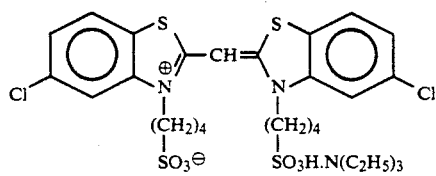

($2.0 \times 10^{-4}$ mol, per mol of the silver halide, for the large-size grain emulsion and $2.5 \times 1^{-4}$ mol for the small-size grain emulsions)

Sensitizing dye C for green-sensitive emulsion layer

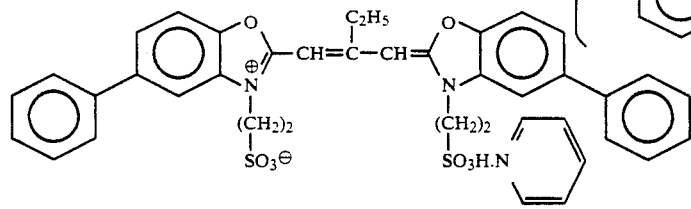

($4.0 \times 10^{-4}$ mol, per mol of the silver halide, for the large-size grain emulsion B and $5.6 \times 10^{-4}$ mol for the small-size grain emulsion B) and Sensitizing dye D for green-sensitive emulsion layer

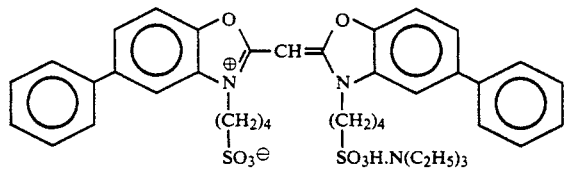

($7.0 \times 10^{-5}$ mol, per mol of the silver halide, for the large-size grain emulsion B and $1.0 \times 10^{-5}$ mol for the small size grain emulsion B)

Sensitizing dye E for red-sensitive emulsion layer

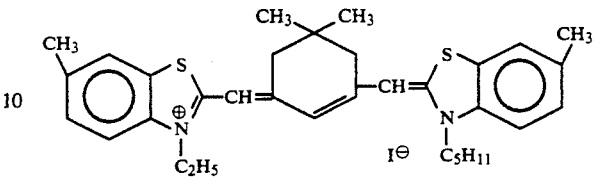

($0.9 \times 10^{-4}$ mol, per mol of the silver halide, for the large-size grain emulsion C and $1.1 \times 10^{-4}$ mol for the small size grain emulsion C)

$2.6 \times 10^{-3}$ mol, per mol of the silver halide, of the following compound was incorporated into the red-sensitive emulsion layer:

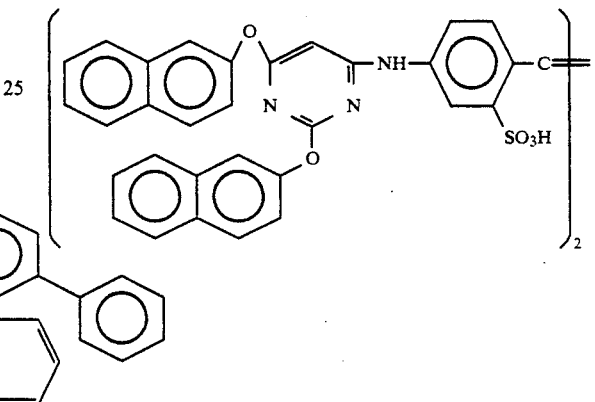

$8.5 \times 10^{-5}$ mol, $7.7 \times 10^{-4}$ mol, per mol of the silver halide, of 1-(5-methylureidophenyl)-5-mercaptotetrazole was incorporated into the blue-sensitive emulsion layer, green-sensitive emulsion layer and red-sensitive emulsion layer, respectively.

$1 \times 10^{-4}$ mol and $2 \times 10^{-4}$ mol, per mol of the silver halide, of 4-hydroxy-6-methyl-1,3,3a,7-tetrazaindene was incorporated into the blue-sensitive emulsion layer and green-sensitive emulsion layer, respectively.

The following dyes were incorporated into the emulsion layers in order to prevent irradiation (numerals in the parentheses are amount used for coating):

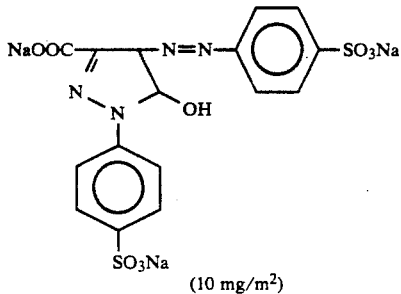

(10 mg/m²)

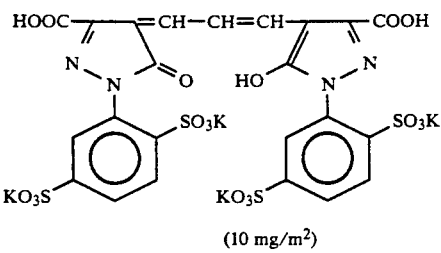

(10 mg/m²)

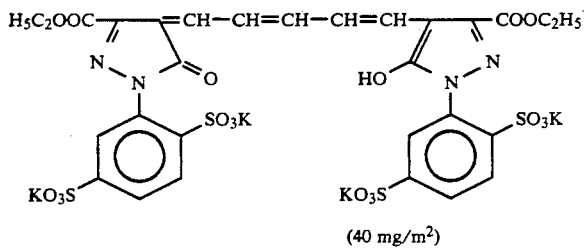

(40 mg/m²)

and

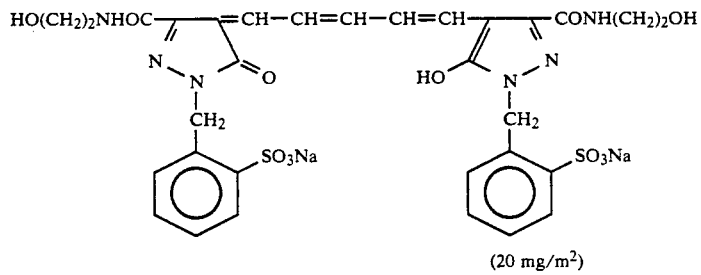

(20 mg/m²)

Layer Construction

The compositions of the respective layers will be shown below. The numerals represent the amount (g/m²) of the components used for forming the layers. The amount of the silver halide emulsion is given in terms of silver used for forming the layer.

Support

Polyethylene-Laminated Paper [Containing a White Dye (TiO₂) and a Blue Dye (Ultramarine) in the Polyethylene Layer on the First Layer Side]

| The first layer (blue-sensitive emulsion layer): | |
| --- | --- |
| Above-described silver chlorobromide emulsion A | 0.30 |
| Gelatin | 1.86 |
| Yellow coupler (ExY) | 0.82 |
| Color image stabilizer (Cpd-1) | 0.19 |
| Solvent (Solv-3) | 0.18 |
| Solvent (Solv-7) | 0.18 |
| Color image stabilizer (Cpd-7) | 0.06 |
| The second layer (color mixing-inhibition layer) | |
| Gelatin | 0.99 |
| Color mixing inhibitor (Cpd-5) | 0.08 |
| Solvent (Solv-1) | 0.16 |
| Solvent (Solv-4) | 0.08 |
| The third layer (green-sensitive emulsion layer) | |
| Silver chlorobromide emulsion [mixture of large-grain size emulsion B of cubic grains having average grain size of 0.55 μm and small-grain size emulsion B having average grain size of 0.39 μm in a molar ratio of 1:3 (in terms of Ag); Coefficient of variation of grain size distribution being 0.10 and 0.08; 0.8 molar % of AgBr being contained in a part of the surface layer of the grains in each emulsion] | 0.12 |
| Gelatin | 1.24 |
| Magenta coupler (ExM) | 0.23 |
| Color image stabilizer (Cpd-2) | 0.03 |
| Color image stabilizer (Cpd-3) | 0.16 |
| Color image stabilizer (Cpd-4) | 0.02 |
| Color image stabilizer (Cpd-9) | 0.02 |
| Solvent (Solv-2) | 0.40 |
| The fourth layer (ultraviolet ray-absorbing layer) | |
| Gelatin | 1.58 |
| Ultraviolet ray-absorbing agent (UV-1) | 0.47 |
| Color mixing-inhibiting agent (Cpd-5) | 0.05 |
| Solvent (Solv-5) | 0.24 |
| The fifth layer (red-sensitive emulsion layer) | |
| Silver chlorobromide emulsion [mixture of large-grain size emulsion C of cubic grains having average grain size of 0.58 μm and small-grain size emulsion C having average grain size of 0.45 μm in a molar ratio of 1:4 (in terms of Ag); Coefficient of variation of grain size distribution being 0.09 and 0.11; 0.6 molar % of AgBr being contained in a part of the surface layer of the grains in each emulsion] | 0.23 |
| Gelatin | 1.34 |
| Cyan coupler (ExC) | 0.32 |
| Color image stabilizer (Cpd-2) | 0.03 |
| Color image stabilizer (Cpd-4) | 0.02 |
| Color image stabilizer (Cpd-6) | 0.18 |
| Color image stabilizer (Cpd-7) | 0.40 |
| Color image stabilizer (Cpd-8) | 0.05 |
| Solvent (Solv-6) | 0.14 |
| The sixth layer (ultraviolet ray-absorbing layer) | |
| Gelatin | 0.53 |
| Ultraviolet ray-absorbing agent (UV-1) | 0.16 |
| Color mixing-inhibitor (Cpd-5) | 0.02 |
| Solvent (Solv-5) | 0.08 |
| The seventh layer (protecting layer) | |
| Gelatin | 1.33 |
| Acryl-modified copolymer of polyvinyl alcohol (degree of modification: 17%) | 0.17 |

| -continued | |
|---|---|
| Liquid paraffin | 0.03 |

(ExY) Yellow Coupler

Mixture of compounds of the following formula:

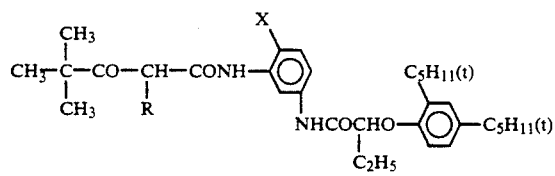

wherein R represents

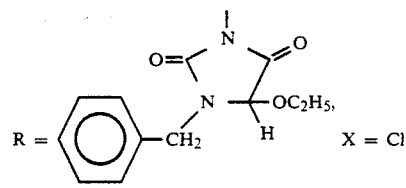

and

R = <image equation> X = OCH₃ in a molar ratio of 1:1

(ExM) Magenta Coupler

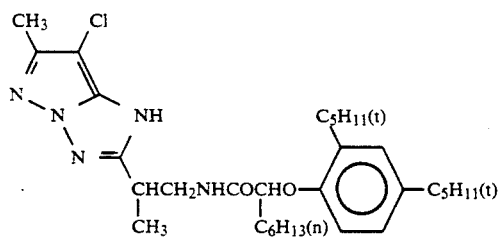

ExC) Cyan Coupler

Mixture of compounds of the following formulae:

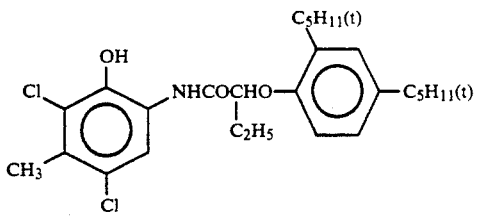

and

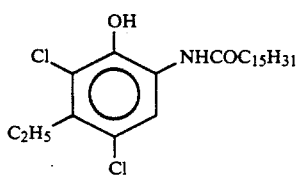

in a molar ratio of 1:1

(Cpd-1) Color Image Stabilizer

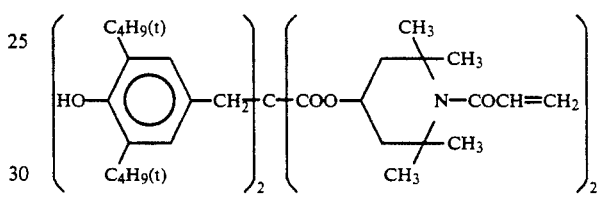

(Cpd-2) Color Image Stabilizer

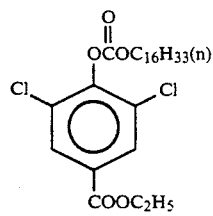

(Cpd-3) Color Image stabilizer

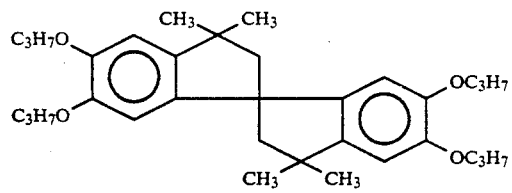

(Cpd-4) Color Image Stabilizer

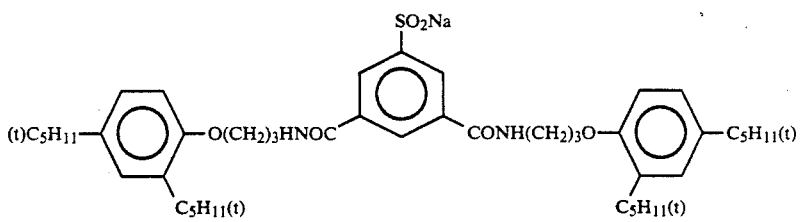

(Cpd-5) Color-Mixing Inhibitor

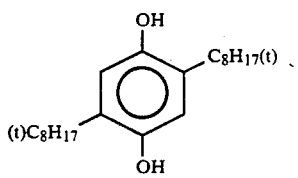

(Cpd-6) Color Image Stabilizer

Mixture of compounds of the following formulae:

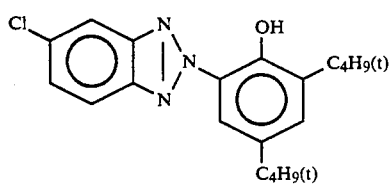

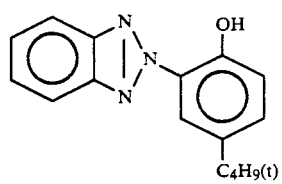

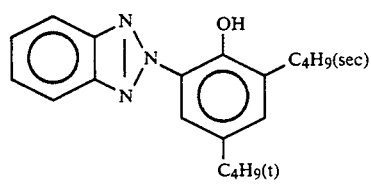

in a weight ratio of 2:4:4.

(Cpd-7) Color Image Stabilizer

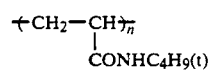

average molecular weight: 60,000

(Cpd-8) Color Image Stabilizer

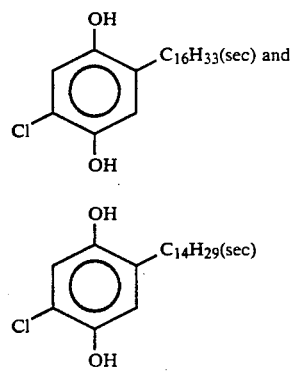

in a weight ratio of 1:1

(Cpd-9) Color Image Stabilizer

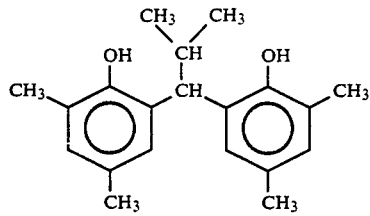

(Cpd-10) Antiseptic

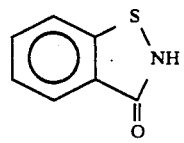

(Cpd-11) Antiseptic

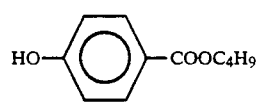

(UV-1) Ultraviolet Ray-Absorbing Agent

Mixture of compounds of the following formulae:

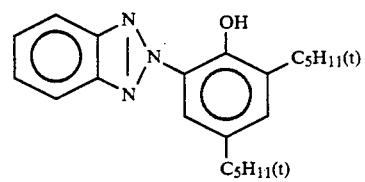

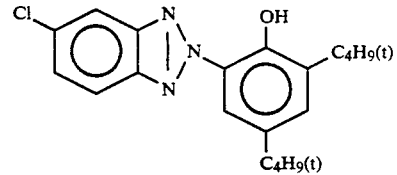

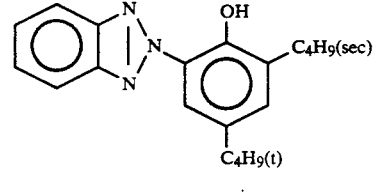

in a weight ratio of 4:2:4.

(Solv-1) Solvent

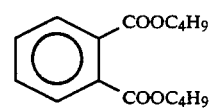

(Solv-2) Solvent

Mixture of compounds of the following formulae:

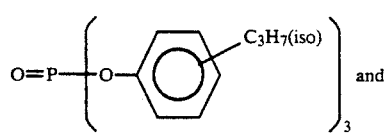

and

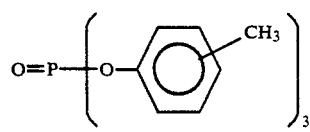

in a volume ratio of 1:1.

(Solv-3) Solvent

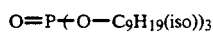

(Solv-4) Solvent

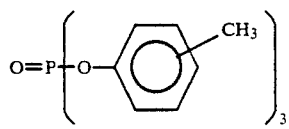

(Solv-5) Solvent

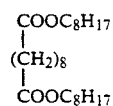

(Solv-6) Solvent

Mixture of compounds of the following formulae:

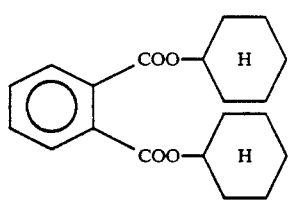

and

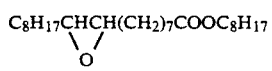

in a volume ratio of 80:20.

(Solv-7) Solvent

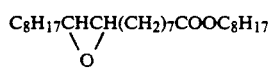

The samples prepared as described above was exposed by an ordinary method.

Then the exposed samples were processed with developers (A) or (B) each containing the developing agent of the present invention, or developers (C) or (D) each containing a comparative developing agent. They were then processed with a bleach-fixing solution and a rinsing solution to form four samples each having a color image.

The photosensitive material prepared as described above was subject to a running test by means of a paper processing machine with processing solutions described below by a process comprising the following steps until a color developer had been replenished in an amount of twice as much as the tank capacity.

| Step | Temp. (°C.) | Time (sec) | Amount of replenisher (per m² of photo sensitive material) (ml) | Tank capacity (l) |
|---|---|---|---|---|
| Color development | 35 | 90 | 161 | 17 |
| Bleach-fixing | 30 to 35 | 45 | 215 | 17 |
| Rinse (1) | 30 to 35 | 20 | — | 10 |
| Rinse (2) | 30 to 25 | 20 | — | 10 |
| Rinse (3) | 30 to 35 | 20 | 350 | 10 |
| Drying | 70 to 80 | 60 | | |

The rinses were used in countercurrent system from the rinse (3) to rinse (1).

The compositions of the processing solutions were as follows:

| Color developer | Mother liquor* | Replenisher |
|---|---|---|
| Water | 800 ml | 800 ml |
| Ethylenediamine-N,N,N,N-tetramethylenephosphonic acid | 1.5 g | 2.0 g |
| Potassium bromide | 0.015 g | — |
| Triethanolamine | 8.0 g | 12.0 g |
| Sodium chloride | 1.4 g | — |
| Potassium carbonate | 25 g | 25 g |
| Developing agent (A), (B), (C) or (D) given below | 7 mmol | 9.5 mmol |
| N,N-Bis(carboxymethyl)-hydrazine | 4.0 g | 5.0 g |
| Monosodium N,N-di(sulfoethyl)-hydroxylamine | 4.0 g | 5.0 g |
| Fluorescent brightener (WHITEX 4B; mfd. by Sumitomo Chemical Co., Ltd.) | 1.0 g | 2.0 g |
| Water | ad 1000 ml | 1000 ml |
| pH (25° C.) | 10.05 | 10.45 |

*Tank solution

Color Developing Agents

Developer (A): p-toluenesulfonate of compound (1) of the present invention

Developer (B): p-toluenesulfonate of compound (9) of the present invention

Developer (C): 4-[N,N-diethylamino]-aniline sulfate

Developer (D): 4-[N-ethyl-N-(β-methanesulfonamidoethyl)amino]-3-methylaniline sulfate

| Bleach-fixing solution: (The mother liquor was the same as the replenisher) | |
|---|---|
| Water | 400 ml |
| Ammonium thiosulfate (70%) | 100 ml |
| Sodium sulfite | 17 g |
| Ferric ammonium ethylenediaminetetraacetate | 55 g |
| Disodium ethylenediaminetetraacetate | 5 g |
| Ammonium bromide | 40 g |
| Water | ad 1000 ml |

-continued

| Bleach-fixing solution: (The mother liquor was the same as the replenisher) | |
|---|---|
| pH (25° C.) | 6.0 |

Rinse (Both Mother Liquor and Replenisher)
Ion-exchanged water (containing less than 3 ppm of calcium and magnesium)

The density of each of the yellow, magenta and cyan of these samples was determined to find that they were sufficient.

The color image stability was examined by 8-day forced fading test with a xenon fading tester (100,000 lx).

The results are shown in terms of density reduction rate at a part of magenta density of 1.0.

| No. | Color developer | Reduction rate (%) | |
|---|---|---|---|
| 2-1 | (A) | 7 | Present invention |
| 2-2 | (B) | 6 | Present invention |
| 2-3 | (C) | 15 | Comparative example |
| 2-4 | (D) | 13 | Comparative example |

It is apparent from the above results that the color images of the samples processed with the developing agent of the present invention had a high fastness.

The fastness of the yellow and cyan parts was also high.

EXAMPLE 2

A photosensitive material was prepared in the same manner as that of Example 1 except that the compositions of the first, third, fifth and sixth layers were altered as follows:

The First Layer

The same as the first layer in Example 1 except that the color image stabilizers (Cpd-1) and (Cpd-7) were omitted.

The Third Layer

The same as the third layer in Example 1 except that the color image stabilizers (Cpd-2), (Cpd-3), (Cpd-4) and (Cpd-9) were omitted.

The Fifth Layer

The same as the fifth layer in Example 1 except that the color image stabilizers (Cpd-2), (Cpd-4), (Cpd-6), (Cpd-7) and (Cpd-8) were omitted.

The Sixth Layer

The same as the sixth layer in Example 1 except that the ultraviolet ray absorber (UV-1) was omitted.

The sample thus prepared was exposed by an ordinary method.

It was then processed with the developer (A), (B), (C) or (D) in the same manner as that of Example 1.

The yellow, magenta and cyan densities of these samples were determined to find that they were satisfactory.

The color image stability was examined by 8-day forced fading test with a xenon fading tester (100,000 lx).

The results were shown in terms of density reduction rate at a part of magenta density of 1.0.

| No. | Color developer | Reduction rate (%) | |
|---|---|---|---|
| 3-1 | (A) | 15 | Present invention |
| 3-2 | (B) | 11 | Present invention |
| 3-3 | (C) | 56 | Comparative example |
| 3-4 | (D) | 50 | Comparative example |

It is apparent from the above results that the color images of the samples processed with the developing agent of the present invention had a fastness higher than those of the samples processed with known comparative developing agents. It is apparent also that the color images formed with the developing agent of the present invention had a substantially enough fastness even without any color image stabilizer.

The fastness of the yellow and cyan parts was also high.

EXAMPLE 3

The sample photosensitive material as that of Example 1 was exposed by an ordinary method.

It was processed in the same manner as that of Example 1 except that the following developers comprising the following color developing agents (E), (F), (G), (H) and (I), respectively, or the coloring agent (D) used in Example 1 were used:

Color Developing Agents

Developer (E) p-toluenesulfonate of compound (11) of the present invention

Developer (F) p-toluenesulfonate of compound (20) of the present invention

Developer (G) p-toluenesulfonate of compound (33) of the present invention

Developer (H) p-toluenesulfonate of compound (35) of the present invention

Developer (I) p-toluenesulfonate of compound (36) of the present invention

The yellow, magenta and cyan densities of these samples were determined to find that they were vivid and satisfactory.

The color image stability was examined by 8-day forced fading test with a xenon fading tester (100,000 lx).

It was found that the color images (all of yellow, magenta and cyan) of the samples processed with the developing agent of the present invention had a fastness higher than those of the samples processed with known comparative developing agent (D).

EXAMPLE 4

Layers of the following compositions were formed on a primed cellulose triacetate film support to form a multi-layered color photosensitive material (Sample 101).

Compositions of Photosensitive Layers

The amounts of the components are given in terms of g/m$^2$ and those of silver halides are given in terms of g/m$^2$ of silver. The amount of sensitizing dyes were given in terms of mol per mol of the silver halide contained in the same layer.

| (Sample 101) |
|---|
| The first layer (antihalation layer): |

(Sample 101)

| | | |
|---|---|---|
| Black colloidal silver | silver | 0.18 |
| Gelatin | | 1.40 |

The second layer (intermediate layer):

| | |
|---|---|
| 2,5-Di-t-pentadecylhydroquinone | 0.18 |
| EX-1 | 0.070 |
| EX-3 | 0.020 |
| EX-12 | $2.0 \times 10^{-3}$ |
| U-1 | 0.060 |
| U-2 | 0.080 |
| U-3 | 0.10 |
| HBS-1 | 0.10 |
| HBS-2 | 0.020 |
| Gelatin | 1.04 |

The third layer (the first red-sensitive emulsion layer)

| | | |
|---|---|---|
| Emulsion A | silver | 0.25 |
| Emulsion B | silver | 0.25 |
| Sensitizing Dye I | | $6.9 \times 10^{-5}$ |
| Sensitizing Dye II | | $1.8 \times 10^{-5}$ |
| Sensitizing Dye III | | $3.1 \times 10^{-4}$ |
| EX-2 | | 0.34 |
| EX-10 | | 0.020 |
| U-1 | | 0.070 |
| U-2 | | 0.050 |
| U-3 | | 0.070 |
| HBS-1 | | 0.060 |
| Gelatin | | 0.87 |

The fourth layer (the second red-sensitive emulsion layer)

| | | |
|---|---|---|
| Emulsion G | silver | 1.00 |
| Sensitizing Dye I | | $5.1 \times 10^{-5}$ |
| Sensitizing Dye II | | $1.4 \times 10^{-5}$ |
| Sensitizing Dye III | | $2.3 \times 10^{-4}$ |
| EX-2 | | 0.40 |
| EX-3 | | 0.050 |
| EX-10 | | 0.015 |
| U-1 | | 0.070 |
| U-2 | | 0.050 |
| U-3 | | 0.070 |
| Gelatin | | 1.30 |

The fifth layer (the third red-sensitive emulsion layer)

| | | |
|---|---|---|
| Emulsion D | silver | 1.60 |
| Sensitizing Dye I | | $5.4 \times 10^{-5}$ |
| Sensitizing Dye II | | $1.4 \times 10^{-5}$ |
| Sensitizing Dye III | | $2.4 \times 10^{-4}$ |
| EX-2 | | 0.097 |
| EX-3 | | 0.010 |
| EX-4 | | 0.080 |
| HBS-1 | | 0.22 |
| HBS-2 | | 0.10 |
| Gelatin | | 1.63 |

The sixth layer (intermediate layer)

| | |
|---|---|
| EX-5 | 0.040 |
| HBS-1 | 0.020 |
| Gelatin | 0.80 |

The seventh layer (the first green-sensitive emulsion layer)

| | | |
|---|---|---|
| Emulsion A | silver | 0.15 |
| Emulsion B | silver | 0.15 |
| Sensitizing Dye IV | | $3.0 \times 10^{-5}$ |
| Sensitizing Dye V | | $1.0 \times 10^{-4}$ |
| Sensitizin Dye VI | | $3.8 \times 10^{-4}$ |
| EX-1 | | 0.021 |
| EX-6 | | 0.26 |
| EX-7 | | 0.030 |
| EX-8 | | 0.025 |
| HBS-1 | | 0.10 |
| HBS-3 | | 0.010 |
| Gelatin | | 0.63 |

The eighth layer (the second green-sensitive emulsion layer)

| | | |
|---|---|---|
| Emulsion C | silver | 0.45 |
| Sensitizing Dye IV | | $2.1 \times 10^{-5}$ |
| Sensitizing Dye V | | $7.0 \times 10^{-5}$ |
| Sensitizing Dye VI | | $2.6 \times 10^{-4}$ |
| EX-6 | | 0.094 |
| EX-7 | | 0.026 |
| EX-8 | | 0.018 |
| HBS-1 | | 0.16 |
| HBS-3 | | $8.0 \times 10^{-3}$ |
| Gelatin | | 0.50 |

The ninth layer (the third green-sensitive emulsion layer)

| | | |
|---|---|---|
| Emulsion E | silver | 1.20 |
| Sensitizing Dye IV | | $3.5 \times 10^{-5}$ |
| Sensitizing Dye V | | $8.0 \times 10^{-5}$ |
| Sensitizing Dye VI | | $3.0 \times 10^{-4}$ |
| EX-1 | | 0.025 |
| EX-11 | | 0.10 |
| EX-13 | | 0.015 |
| HBS-1 | | 0.25 |
| HBS-2 | | 0.10 |
| Gelatin | | 1.54 |

The tenth layer (yellow filter layer)

| | | |
|---|---|---|
| Yellow colloidal silver | silver | 0.050 |
| EX-5 | | 0.080 |
| HBS-1 | | 0.030 |
| Gelatin | | 0.95 |

The eleventh layer (the first blue-sensitive emulsion layer)

| | | |
|---|---|---|
| Emulsion A | silver | 0.080 |
| Emulsion B | silver | 0.070 |
| Emulsion F | silver | 0.070 |
| Sensitizing Dye VII | | $3.5 \times 10^{-4}$ |
| EX-8 | | 0.042 |
| EX-9 | | 0.72 |
| HBS-1 | | 0.28 |
| Gelatin | | 1.10 |

The twelfth layer (the second blue-sensitive emulsion layer)

| | | |
|---|---|---|
| Emulsion G | silver | 0.45 |
| Sensitizing Dye VII | | $2.1 \times 10^{-4}$ |
| EX-9 | | 0.15 |
| EX-10 | | $7.0 \times 10^{-3}$ |
| HBS-1 | | 0.050 |
| Gelatin | | 0.78 |

The thirteenth layer (the third blue-sensitive emulsion layer)

| | | |
|---|---|---|
| Emulsion H | silver | 0.77 |
| Sensitizing Dye VII | | $2.2 \times 10^{-4}$ |
| EX-9 | | 0.20 |
| HBS-1 | | 0.070 |
| gelatin | | 0.69 |

The fourteenth layer (the first protecting layer)

| | | |
|---|---|---|
| Emulsion I | silver | 0.20 |
| U-4 | | 0.11 |
| U-5 | | 0.17 |
| HBS-1 | | $5.0 \times 10^{-2}$ |
| Gelatin | | 1.00 |

The fifteenth layer (the second protecting layer)

| | |
|---|---|
| H-1 | 0.40 |
| B-1 (diameter: 1.7 μm) | $5.0 \times 10^{-2}$ |
| B-2 (diameter: 1.7 μm) | 0.10 |
| B-3 | 0.10 |
| S-1 | 0.20 |
| Gelatin | 1.20 |

Further, W-1, W-2, W-3, B-4, B-5, F-1, F-2, F-3, F-4, F-5, F-6, F-7, F-8, F-9, F-10, F-11, F-12 and F-13 as well as an iron salt, lead salt, gold salt, platinum salt, iridium salt and rhodium salt were incorporated into all the layers in order to improve the storability, processability, pressure resistance, mildew resistance, antimicrobial properties, antistatic properties and spreadability.

| Emulsion | Average AgI content (%) | Average grain diameter (μm) | Coefficient of variation of grain diameter (%) | Diameter/ thickness ratio | Silver amount ratio (AgI content %) |
|---|---|---|---|---|---|
| A | 4.0 | 0.45 | 27 | 1 | Core/shell = 1 (13/1), double structure grains |
| B | 8.9 | 0.70 | 14 | 1 | Core/shell = 3/7 (25/2), double structure |

| Emulsion | Average AgI content (%) | Average grain diameter (μm) | Coefficient of variation of grain diameter (%) | Diameter/ thickness ratio | Silver amount ratio (AgI content %) |
|---|---|---|---|---|---|
| C | 10 | 0.75 | 30 | 2 | grains Core/shell = ½ (24/3), double structure grains |
| D | 16 | 1.05 | 35 | 2 | Core/shell = 4/6 (40/0), double structure grains |
| E | 10 | 1.05 | 35 | 3 | Core/shell = ½ (24/3), double structure grains |
| F | 4.0 | 0.25 | 28 | 1 | Core/shell = ⅛ (13/1), double structure grains |
| G | 14.0 | 0.75 | 25 | 2 | Core/shell = ½ (42/0), double structure grains |
| H | 14.5 | 1.30 | 25 | 3 | Core/shell = 37/63(34/3) double structure grains |
| I | 1 | 0.07 | 15 | 1 | Homogeneous grains |

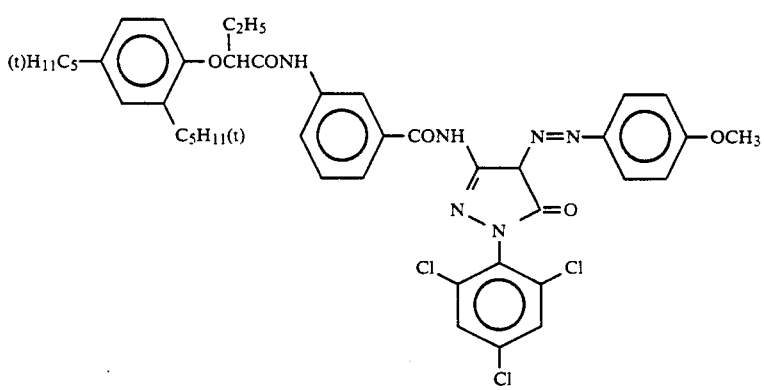

EX-1

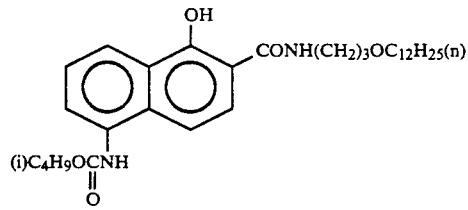

EX-2

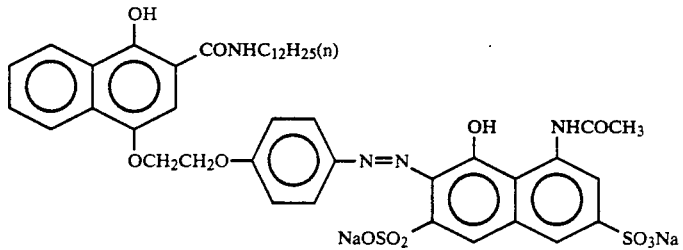

EX-3

EX-4          EX-5

-continued
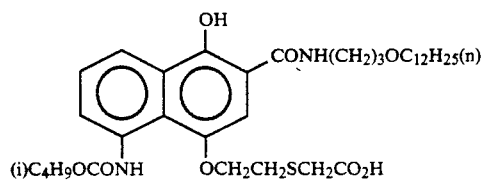
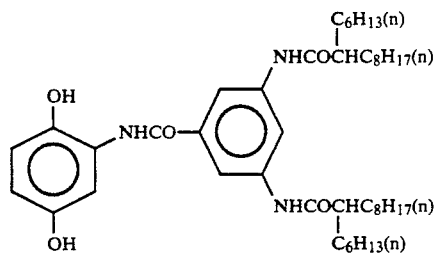
EX-6
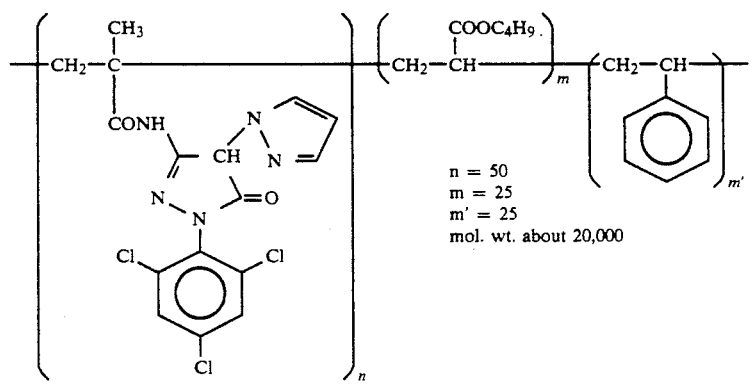
EX-7
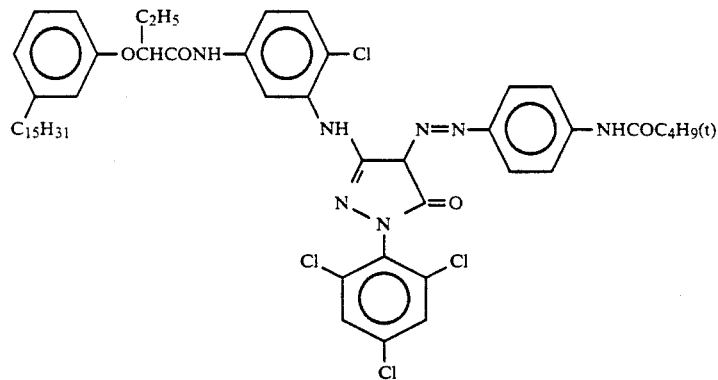
EX-8
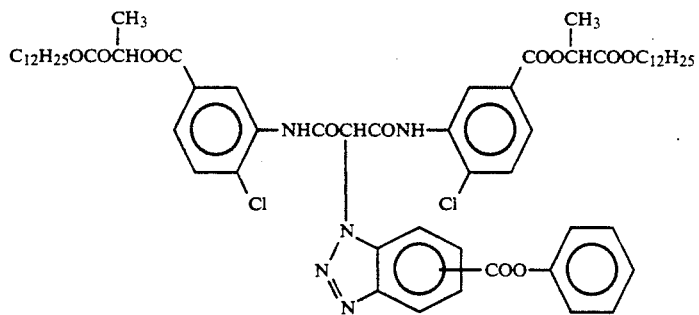
EX-9

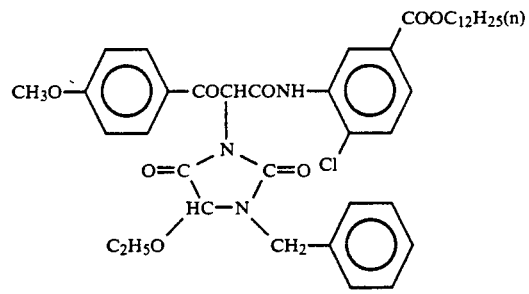
EX-10
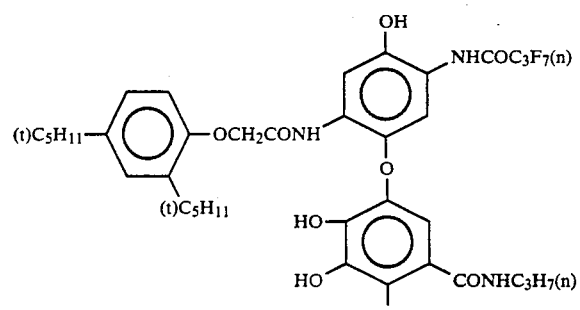
EX-11
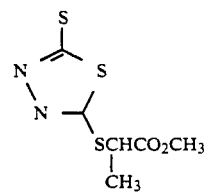
EX-12
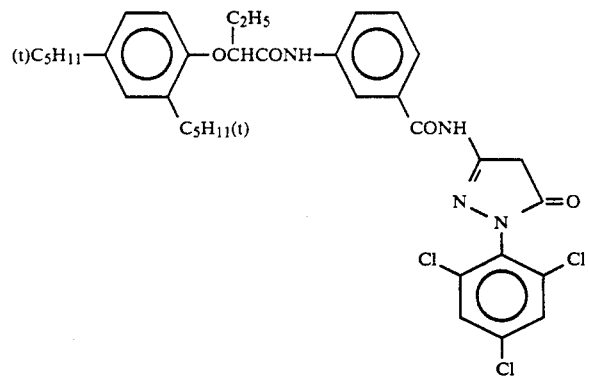
EX-13
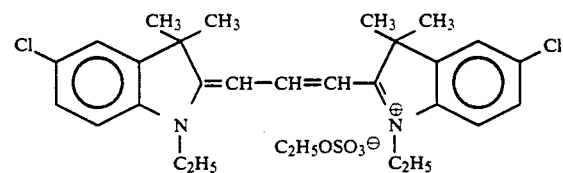

-continued
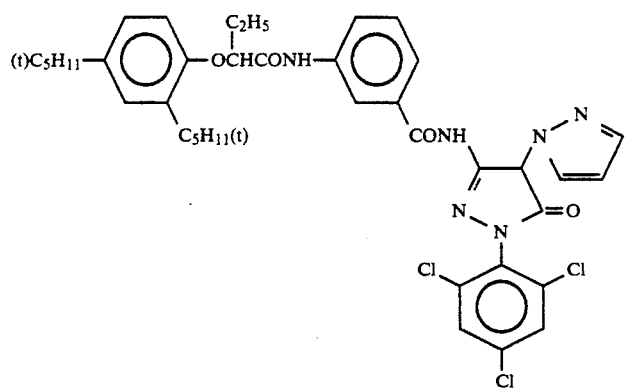
U-1
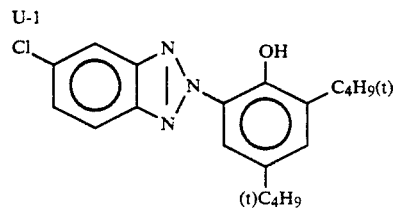
U-2
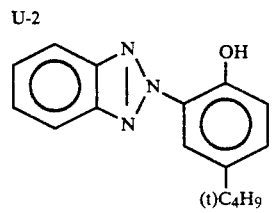
U-3
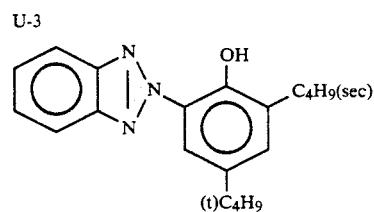
U-4
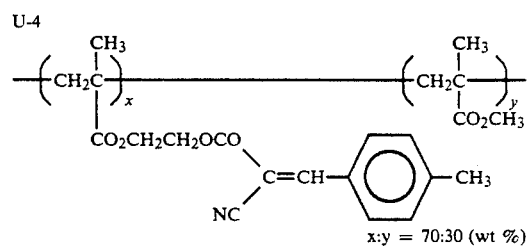
U-5
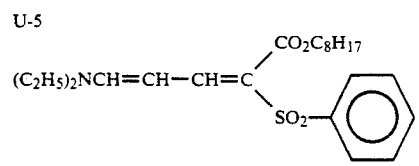
UBS-1
Tricresyl phosphate
UBS-2
Di-n-butyl phthalate
UBS-3
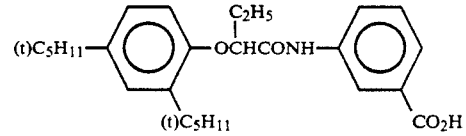
Sensitizing dye I
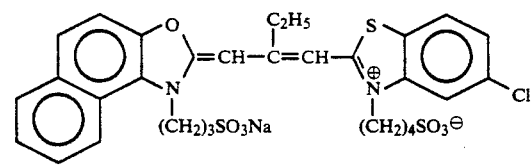
Sensitizing dye II
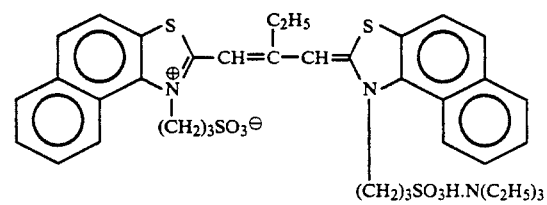
Sensitizing dye III
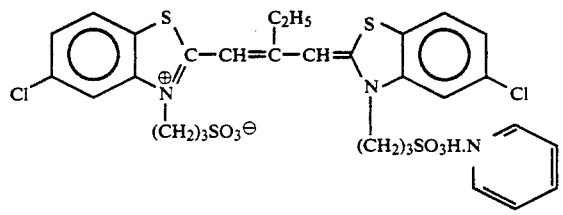

Sensitizing dye IV
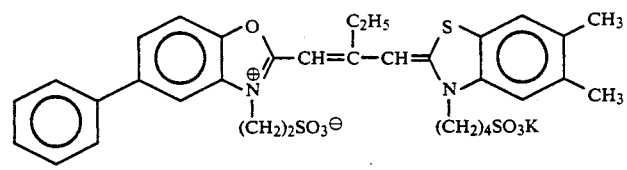
Sensitizing dye V
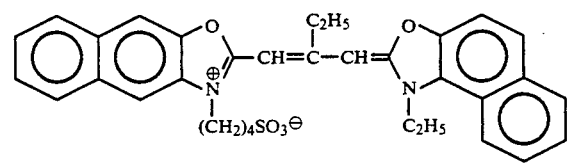
Sensitizing dye VI
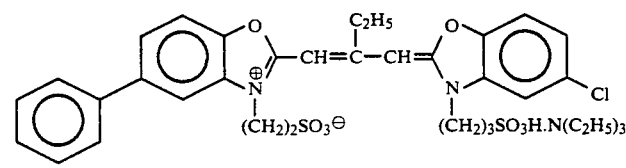
Sensitizing dye VII
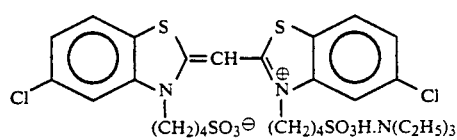
S-1
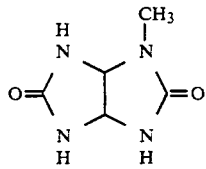
H-1
$CH_2=CH-SO_2-CH_2-CONH-CH_2$
$CH_2=CH-SO_2-CH_2-CONH-CH_2$
B-1
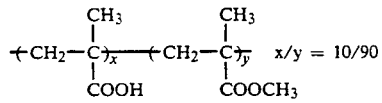 x/y = 10/90
B-2
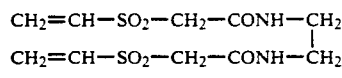 x/y = 40/60
B-3
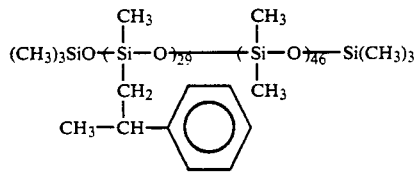
B-4
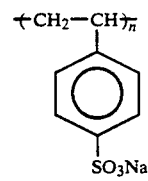
B-5
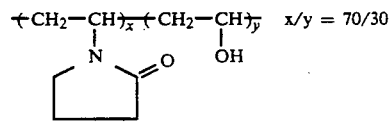 x/y = 70/30
W-1
$C_8F_{17}SO_2NHCH_2CH_2CH_2OCH_2CH_2\overset{\oplus}{N}(CH_3)_3$
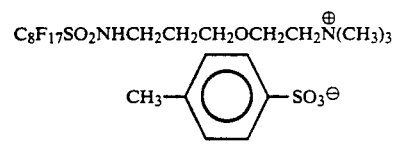
W-2
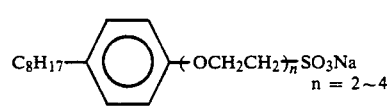 n = 2~4
W-3
F-1

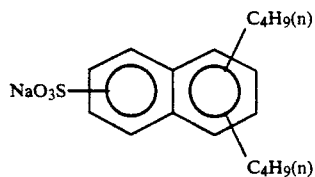

F-2
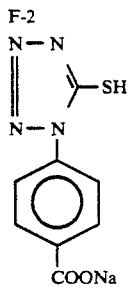

F-4
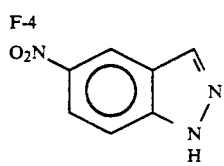

F-6
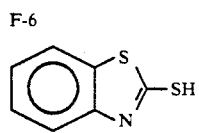

F-8
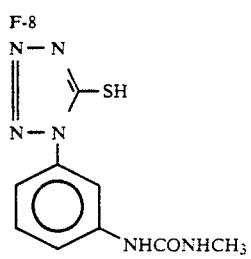

F-10
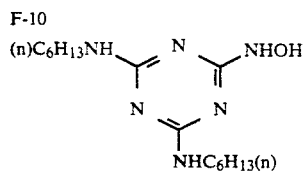

F-12
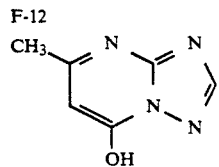

-continued
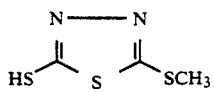

F-3
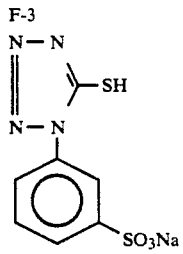

F-5
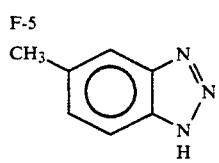

F-7
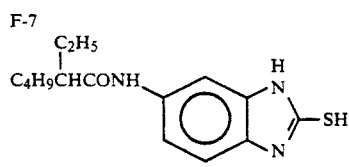

F-9
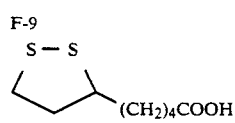

F-11
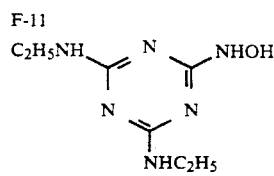

F-13
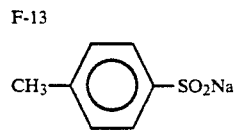

The samples thus prepared were exposed by an ordinary method.

They were then processed with one of four kinds of developers, i.e. developers (J) and (K) each containing the developing agent of the present invention and developers (L) and (M) each containing a comparative developing agent given below. After subjecting to the processes with a bleaching solution, bleach-fixing solution and stabilizing solution, four kinds of samples having color images were obtained.

| Step | Process Time | Temp. | Amount of replenisher | Capacity of tank |
|---|---|---|---|---|
| Color development | 6 min 30 sec | 37.8° C. | 25 ml | 10 l |
| Bleaching | 45 sec | 38° C. | 5 ml | 4 l |
| Bleach-fixing (1) | 45 sec | 38° C. | — | 4 l |
| Bleach- | 45 sec | 38° C. | 30 ml | 4 l |

-continued

| | Process | | | |
|---|---|---|---|---|
| Step | Time | Temp. | Amount of replenisher | Capacity of tank |
| fixing (2) | | | | |
| Washing with water (1) | 20 sec | 38° C. | — | 2 l |
| Washing with water (2) | 20 sec | 38° C. | 30 ml | 2 l |
| Stabilization | 20 sec | 38° C. | 20 ml | 2 l |
| Drying | 1 min | 55° C. | | |

The amount of replenisher is given per 35 mm width and 1 - length.

The bleach fixing solutions and water for washing flowed countercurrently from step (2) to step (1) and the overflowed bleaching solution was introduced into the bleach-fixing step (2).

The amount of the bleach-fixing solution taken into the step of washing with water was 2 ml per m of the photosensitive material having a width of 35 mm.

| (Color developer) | Mother liquor (g) | Replenisher (g) |
|---|---|---|
| Diethylenetriaminepentaacetic acid | 5.0 | 6.0 |
| Sodium sulfite | 4.0 | 5.0 |
| Potassium carbonate | 30.0 | 37.0 |
| Potassium bromide | 1.3 | 0.5 |
| Potassium iodide | 1.2 mg | — |
| Hydroxylamine sulfate | 2.0 | 3.6 |
| Developing agent (J), (K), (L) or (M) given below | 6.5 mmol | 8.5 mmol |
| Water | ad 1.0 l | 1.0 l |
| pH | 10.00 | 10.15 |

Color Developing Agents

Developer (J) p-toluenesulfonate of compound (1) of the present invention

Developer (K) p-toluenesulfonate of compound (8) of the present invention

Developer (L) 4-[N,N-diethylamino]-aniline sulfate

Developer (M) 4-[N-ethyl-N-$\beta$-hydroxyethylamino]-2-methylaniline sulfate

| (Bleaching solution) | Mother liquor (g) | Replenisher (g) |
|---|---|---|
| Ferric ammonium 1,3-diaminopropane tetraacetate monohydrate | 144.0 | 206.0 |
| 1,3-Diaminopropanetetraacetic acid | 2.8 | 4.0 |
| Ammonium bromide | 84.0 | 120.0 |
| Ammonium nitrate | 17.5 | 25.0 |
| Aqueous ammonia (27%) | 10.0 | 1.8 |
| Acetic acid (98%) | 51.1 | 73.0 |
| Water | ad 1.0 l | 1.0 l |
| pH | 4.3 | 3.4 |

| (Bleach-fixing solution) | Mother liquor (g) | Replenisher (g) |
|---|---|---|
| Ferric ammonium ethylenediaminetetraacetate dihydrate | 50.0 | — |
| Disodium ethylenediaminetetraacetate | 5.0 | 25.0 |
| Ammonium sulfite | 12.0 | 20.0 |
| Aqueous ammonium thiosulfate solution (700 g/l) | 290.0 ml | 320.0 ml |
| Aqueous ammonia (27%) | 6.0 ml | 15.0 ml |
| Water | ad 1.0 l | 1.0 l |
| pH | 6.8 | 8.0 |

Washing Water [Both Mother Liquor and Replenisher (g)]

City water was passed through a column of a mixed-bed system filled with H-type strong acidic cation exchange resin (Amberlite IR-120B; product of Rohm & Haas Co.) and OH-type strong basic anion exchange resin (Amberlite IR-400; product of Rohm & Haas Co.) to reduce calcium and magnesium ion concentration to 3 mg/1 l or less. Then 20 mg/l of sodium dichloroisocyanurate and 150 mg/l of sodium sulfate were added thereto. The pH of the liquid was in the range of 6.5 to 7.5.

| (Stabilizing solution) [Both mother liquor and replenisher] (g) | |
|---|---|
| Formalin (37%) | 1.2 ml |
| Surfactant [$C_{10}H_{21}$—O—(—$CH_2 CH_2 O$—)$_{10}$—H] | 0.4 |
| Ethylene glycol | 1.0 |
| Water | ad 1.0 l |
| pH | 5.0 to 7.0 |

The yellow, magenta and cyan densities of these samples were determined to find that they were vivid and sufficient.

The samples were irradiated with a light of a luminescent lamp (17,000 lx) for 7 days to examine the stability of the color images.

It was found that the yellow, magenta and cyan color images of the samples treated with the developing agent of the present invention had a high fastness.

EXAMPLE 5

A photosensitive material described in Example 5 of Japanese Patent Application No. 2-43792 (U.S. Ser. No. 658892) was prepared. It was exposed and further processed in the same manner as that of Example 5 except that the developing agent in the color developer was replaced with an equimolor amount of color developer (N) or (O) or comparative color developer (P) or (Q):

Color Developing Agent

Developer (N) p-toluenesulfonate of compound (8) of the present invention

Developer (O) p-toluenesulfonate of compound (9) of the present invention

Developer (P) p-toluenesulfonate of N-ethyl-N-(2-methoxyethyl)-3-methyl-4-aminoaniline Developer (Q) N-ethyl-($\beta$-methanesulfonamidoethyl)-3-methyl-4-aminoaniline sulfate (described in Japanese Patent Application No. 2-43792).

The samples were irradiated with a light of a luminescent lamp 17,000 lx) for 7 days to examine the stability of the color images.

It was found that the yellow, magenta and cyan color images of the samples processed with the developing agent of the present invention had a fastness higher than that of the samples processed with the known comparative developing agent.

EXAMPLE 6

Sample III-A$_1$ described in Example 6 of J.P. KOKAI No. 62-209457 was prepared. It was exposed and further processed in the same manner as that of Example 6 except that the developing agent in the color developer was replaced with an equimolor amount of color developer (R), (S), (T) or (U) given below:

Color Developing Agent

Developer (R) p-toluenesulfonate of compound (8) of the present invention

Developer (S) p-toluenesulfonate of compound (9) of the present invention

Developer (T) p-toluenesulfonate of N-ethyl-N-(2-methoxyethyl)-3-methyl-4-aminoaniline Developer (U) N-ethyl-N-[2-(methanesulfonamido)ethyl]-3-methyl4-aminoaniline sulfate (described in J.P. KOKAI No. 62-209457)

The densities of the yellow, magenta and cyan color images of the samples thus obtained were determined to find that they were vivid and sufficient.

The stability of the color images was examined by 8 days forced test with a xenon fading tester (100,000 lx).

The results are given in terms of density reduction rate at a part of magenta density of 1.0.

| No. | Color developer | Reduction rate (%) | |
|-----|-----------------|--------------------|-----|
| 5-1 | (R) | 7 | Present invention |
| 5-2 | (S) | 8 | Present invention |
| 5-3 | (T) | 12 | Comparative example |
| 5-4 | (U) | 13 | Comparative example |

It is apparent from the above results that the color images of the samples processed with the developing agent of the present invention had a fastness higher than those of the samples processed with known comparative developing agents.

The fastness of the yellow and cyan parts was also high.

EXAMPLE 7

A photosensitive material described in Example 3 of Japanese Patent Application No. 2-43792 was prepared. It was exposed and further processed in the same manner as that of Example 3 except that the developing agent in the developer was replaced with an equimolor amount of that contained in color developer (V), (W), (X) or (Y) given below:

Color Developing Agent

Developer (V) p-toluenesulfonate of compound (1) of the present invention

Developer (W) p-toluenesulfonate of compound (8) of the present invention

Developer (X) p-toluenesulfonate of compound (9) of the present invention

Developer (Y) N-ethyl-N-($\beta$-methanesulfonamidoethyl)-3-methyl4-aminoaniline sulfate (described in Japanese Patent Application No. 2-43792)

The densities of the yellow, magenta and cyan color images of the examples thus obtained were determined to find that they were vivid and sufficient.

The stability of the color images was examined by 8 days forced fading test with a xenon fading tester (100,000 lx).

It was found that the color images of the samples processed with the developing agent of the present invention had a fastness higher than those of the samples processed with known comparative developing agents.

EXAMPLE 8

Photosensitive materials ($\alpha$) and ($\beta$) were prepared in the same manner as that described in Example 7 of Japanese Patent Application No. 1-96619 (JP KOKAI No. 2-275446, EP 393523A) except that the precursor of the developing agent was replaced with the following compound.

Precursor of Developing Agent

Sample ($\alpha$): Compound (52) of the present invention

Sample ($\beta$):

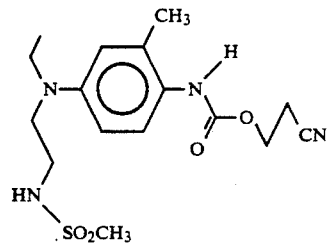

The samples prepared as described above were exposed and processed by a method described in Japanese Patent Application No. 1-96619.

The densities of the yellow, magenta and cyan color images of the samples thus obtained were determined to find that they were sufficient.

The stability of the color images was examined by 8 days forced fading test with a xenon fading tester (100,000 lx).

The results are given in terms of density reduction rate at a part of magenta density of 1.0.

| No. | Color developer | Reduction rate (%) | |
|-----|-----------------|--------------------|-----|
| 7-1 | ($\alpha$) | 10 | Present invention |
| 7-2 | ($\beta$) | 21 | Comparative example |

It is apparent from the above results that the color images of the samples processed with the developing agent of the present invention had a fastness higher than that of the samples processed with known comparative developing agent.

The fastness of the yellow and cyan parts was also high.

EXAMPLE 9

Photosensitive materials (I) and (II) were prepared in the same manner as that described in Example 8 of Japanese Patent Application No. 1-96619 except that the developing agent was replaced with the following compound.

DEVELOPING AGENT

Sample (I): Compound (39) of the present invention

Sample (II):

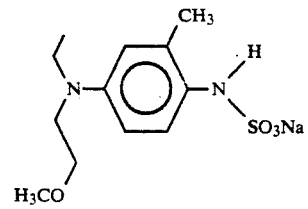

The samples prepared as described above were subjected to thermal development/transfer with the same image-receiving member and in the same manner as those in Example 8 of Japanese Patent Application No. 1-96619.

In the image-receiving member, a step wedge negative image of vivid yellow was formed.

The yellow density of the sample was sufficient.

The stability of the color images was examined by 8 days forced fading test with a xenon fading tester (100,000 lx).

The results are given in terms of density reduction rate at a part of yellow density of 1.0.

| No. | Sample | Reduction rate (%) | |
|---|---|---|---|
| 8-1 | (I) | 25 | Present invention |
| 8-2 | (II) | 31 | Comparative example |

It is apparent from the above results that the color images of the samples processed with the precursor of the developing agent of the present invention had a fastness higher than that of the samples processed with known comparative developing agent.

EXAMPLE 10

Photosensitive materials (III) and (IV) were prepared in the same manner as that described in Example 9 of Japanese Patent Application No. 1-96619 except that the developing agent was replaced with the following compound.

Developing Agent

Sample (III): Compound (39) of the present invention
Sample (IV):

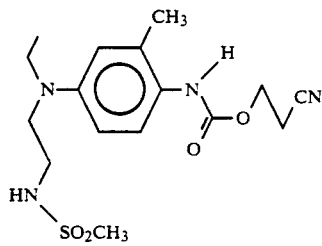

The photosensitive materials prepared as described above were subjected to exposure and thermal development in the same manner as that of Japanese Patent Application No. 1-96619.

The densities of the yellow, magenta and cyan color images of the samples thus obtained were determined to find that they were sufficient.

The stability of the color images was examined by 8 days forced fading test with a xenon fading tester (100,000 lx).

The results are given in terms of density reduction rate at a part of magenta density of 1.0.

| No. | Sample | Reduction rate (%) | |
|---|---|---|---|
| 9-1 | (III) | 25 | Present invention |
| 9-2 | (IV) | 60 | Comparative example |

It is apparent from the above results that the color images of the samples processed with the precursor of the developing agent of the present invention had a fastness higher than that of the samples processed with the known comparative precursor of developing agent.

The fastness of the yellow and cyan images was also high.

As it clear from the afore-description, the stability (such as light stability) of cyan, magenta and yellow dye images can be remarkably improved, by using the new developing agent of the present invention.

Also by using the developing agent of the present invention, fading can be quite effectively prevented, since an image-wise fading-inhibiting effect can be obtained.

What is claimed is:

1. A process for forming an image which comprises color-developing an image-wise exposed silver halide color photographic photosensitive material in the presence of a p-phenylenediamine color developing agent represented by the following general formula (I):

$$A\text{—}(\text{—}L\text{—}B)_q \quad (I)$$

wherein A represents a p-phenylenediamine color developing agent residue derived from the compound represented by the following formula (II):

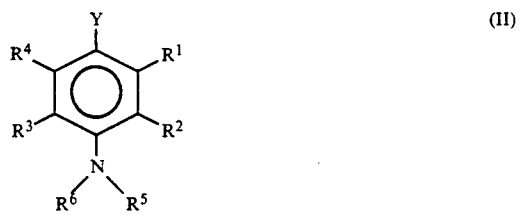

wherein $R^1$, $R^2$, $R^3$ and $R^4$ may be the same or different from one another and each represent a hydrogen atom or a non-metallic substituent, and $R^5$ and $R^6$ may be the same or different and each represent a hydrogen atom or an alkyl, aryl or heterocyclic group, and Y represents $-NH_2$, $-NHY^1$ or $-N=Y^2$, $Y^1$ represents $-SO_3H$, $-SO_3Na$, $-SO_2-R^{21}$,

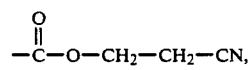

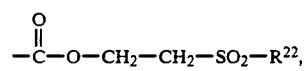

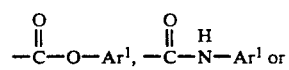

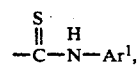

$R^{21}$ and $R^{22}$ may be the same or different and each represent an alkyl group or aryl group, $Ar^1$ represents an aryl group, $Y^2$ represents

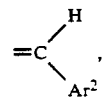

and $Ar^2$ represents an aryl group, and $R^1$ and $R^2$ and/or $R^2$ and $R^5$ and/or $R^5$ and $R^6$ and/or $R^3$ and $R^6$ and/or $R^3$ and $R^4$ may bond together to form a ring structure, L represents a divalent connecting group or a mere bond, B represents an atomic group capable of inhibiting fading of a dye formed by the color developing agent of the formula (I) with a coupler compound q represents an integer of 1 to 3, and when q is 2 or 3, L—B may be the same or different from one another, and B is bonded to A through $R^1$, $R^2$, $R^3$, $R^4$, $R^5$ and $R^6$ and through L.

2. A process for forming an image of claim 1 which comprises color-developing an image-wise exposed silver halide color photographic photosensitive material in the presence of a p-phenylenediamine color developing agent represented by the following general formula (I-α):

$$A-(-L-B)_q \quad (I\text{-}\alpha)$$

wherein A represents a p-phenylenediamine color developing agent residue derived from the compound represented by the following formula (II)

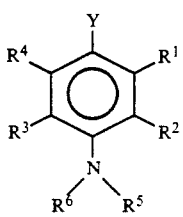

wherein $R^1$, $R^2$, $R^3$ and $R^4$ may be the same or different from one another and each represent a hydrogen atom or a non-metallic substituent, and $R^5$ and $R^6$ may be the same or different and each represent a hydrogen atom or an alkyl, aryl or heterocyclic group, and Y represents $-NH_2$, $-NHY^1$ or $-N=Y^2$, $Y^1$ represents $-SO_3H$, $-SO_3Na$, $-SO_2-R^{21}$,

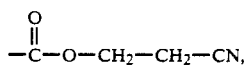

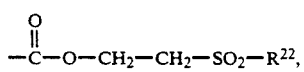

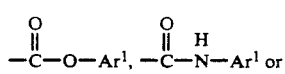

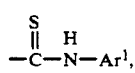

$R^{21}$ and $R^{22}$ may be the same or different and each represent an alkyl group or aryl group, $Ar^1$ represents an aryl group, $Y^2$ represents

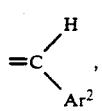

and $Ar^2$ represents an aryl group, and $R^1$ and $R^2$ and/or $R^2$ and $R^5$ and/or $R^5$ and $R^6$ and/or $R^3$ and $R^6$ and/or $R^3$ and $R^4$ may bond together to form a ring structure, B represents a monovalent group derived from a compound represented by the following formula (III):

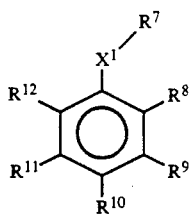

wherein $R^7$ represents an alkyl, $X^1$ represents $-O-$ or $-NR^{13}-$ ($R^{13}$ being a hydrogen atom or an alkyl); $R^8$, $R^9$, $R^{10}$, $R^{11}$, and $R^{12}$ each represents a hydrogen atom or a non-metallic substituent, provided that at least one of the $R^8$ and $R^{10}$ is $-X^1-R^7$, adjacent two groups of $R^8$, $R^9$, $R^{10}$, $R^{11}$ and $R^{12}$ may bond together to form a ring structure, L represents a divalent connecting group or mere bond, q represents an integer of 1 to 3, and when q is 2 or 3, L—B may be the same or different from one another, wherein B is bonded to A through $R^1$, $R^2$, $R^3$, $R^4$, $R^5$ and $R^6$ and through L and A is bonded to B through $R^7$, $R^8$, $R^9$, $R^{10}$, $R^{11}$, $R^{12}$, and through L.

3. A process for forming an image of claim 2 wherein $R^1$, $R^2$, $R^3$ and $R^4$ each represent a hydrogen atom, halogen atom, amino group, alkyl group, aryl group, heterocyclic group, cyano group, nitro group, hydroxyl group, carboxyl group, alkoxyl group, aryloxy group, acylamino group, alkylamino group, anilino group, ureido group, sulfamoylamino group, alkythio group, arylthio group, alkoxycarbonylamino group, sulfonamido group, carbamoyl group, sulfamoyl group, sulfonyl group, alkoxycarbonyl group, heterocyclic-oxy group, azo group, acyloxy group, carbamoyloxy group, silyl group, silyloxy group, arloxycarbonylamino group, imido group, heterocyclic thio group, sulfinyl group, phosphonyl group, sulfo group, aryloxycarbonyl group or acyl group.

4. A process for forming an image of claim 2 wherein $R^1$, $R^2$, $R^3$, $R^4$ each represent a hydrogen atom, alkyl, alkoxyl, alkoxylcarbonylamino and ureido groups, $R^5$ and $R^6$ each represent a substituted or unsubstituted alkyl group having 1 to 16 carbon atoms, and Y represents $-NH_2$.

5. A process for forming an image of claim 3 wherein $R^7$ is an alkyl, $R^8$, $R^9$, $R^{10}$, $R^{11}$, and $R^{12}$ are each a hydrogen atom, $-X^1-R^7$, alkyl, alkenyl, aryl, aryloxycarbonyl, or alkoxycarbonyl group, halogen atom or acyl, sulfonyl, carbamoyl, acylamino, sulfamoyl, cyano, nitro, sulfo or carboxyl group and $X^1$ is $-O-$.

6. A process for forming an image of claim 2 wherein the color developing agent is represented by the following formula (XI):

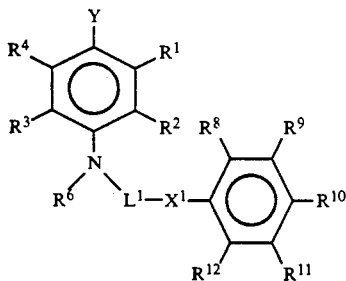
(XI)

wherein $R^1$, $R^2$, $R^3$ and $R^4$ each represent a hydrogen atom, halogen atom, amino group, alkyl group, aryl group, heterocyclic group, cyano group, nitro group, hydroxyl group, carboxyl group, alkoxyl group, aryloxy group, acylamino group, alkylamino group, anilino group, ureido group, sulfamoylamino group, alkylthio group, arylthio group, alkoxycarbonylamino group, sulfonamido group, carbamoyl group, sulfamoyl group, sulfonyl group, alkoxycarbonyl group, heterocyclic-oxy group, azo group, acyloxy group, carbamoyloxy group, silyl group, silyloxy group, aryloxycarbonylamino group, imido group, heterocyclic thio group, sulfinyl group, phosphonyl group, sulfo group, aryloxycarbonyl group or acyl group, $R^6$ represents a hydrogen atom or an alkyl, aryl or heterocyclic group, $X^1$ is —O— or —$NR^{13}$—, $R^8$, $R^9$, $R^{10}$, $R^{11}$ and $R^{12}$ are each a hydrogen atom, alkyl, alkenyl, aryl, aryloxycarbonyl or alkoxycarbonyl group provided that at least one of $R^8$ and $R^{10}$ is —$X^1$—$R^7$ ($X^1$ is —O— or —$NR^{13}$—), $R^7$ is an alkyl and $R^{13}$ is a hydrogen or alkyl, and $L^1$ represents a substituted or unsubstituted alkylene group having 1 to 8 carbon atoms, and Y represents —$NH_2$, —$NHY^1$ or —$N{=}Y^2$, $Y^1$ represents —$SO_3H$, —$SO_3Na$, —$SO_2$—$R^{21}$,

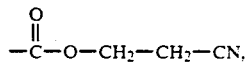

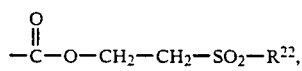

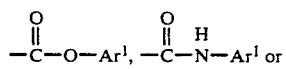

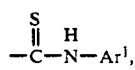

$R^{21}$ and $R^{22}$ may be the same or different and each represent an alkyl group or aryl group, $Ar^1$ represents an aryl group, $Y^2$ represents

and $Ar^2$ represents an aryl group.

7. A process for forming an image of claim 2 wherein the color developing agent is represented by the following formula (XII):

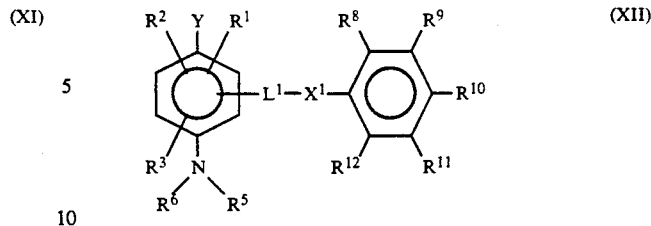
(XII)

wherein $R^1$, $R^2$, and $R^3$ each represent a hydrogen atom, halogen atom, amino group, alkyl group, aryl group, heterocyclic group, cyano group, nitro group, hydroxyl group, carboxyl group, alkoxyl group, aryloxy group, acylamino group, alkylamino group, anilino group, ureido group, sulfamoylamino group, alkylthio group, arylthio group, alkoxycarbonylamino group, sulfonamido group, carbamoyl group, sulfamoyl group, sulfonyl group, alkoxycarbonyl group, heterocyclic-oxy group, azo group, acyloxy group, carbamoyloxy group, silyl group, silyloxy group, aryloxycarbonylamino group, imido group, heterocyclic thio group, sulfinyl group, phosphonyl group, sulfo group, aryloxycarbonyl group or acyl group, $R^5$ and $R^6$ represents a hydrogen atom or an alkyl, aryl or heterocyclic group, $X^1$ is —O— or —$NR^{13}$—, $R^8$, $R^9$, $R^{10}$, $R^{11}$ and $R^{12}$ are each a hydrogen atom, alkyl, alkenyl, aryl, aryloxycarbonyl or alkoxycarbonyl group provided that at least one of $R^8$ and $R^{10}$ is —O—$R^7$ or —$NR^{13}$—, ($R^7$ is an alkyl and $R^{13}$ is a hydrogen or alkyl), $L^1$ represents a substituted or unsubstituted alkylene group having 1 to 8 carbon atoms, and Y represents —$NH_2$, —$NHY^1$ or —$N{=}Y^2$, $Y^1$ represents —$SO_3H$, —$SO_3Na$, —$SO_2$—$R^{21}$

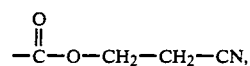

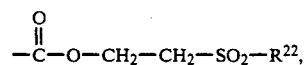

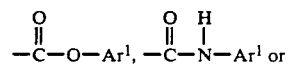

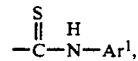

$R^{21}$ and $R^{22}$ may be the same or different and each represent an alkyl group or aryl group, $Ar^1$ represents an aryl group, $Y^2$ represents

and $Ar^2$ represents an aryl group.

8. A process for forming an image of claim 1 which comprises color-developing an image-wise exposed silver halide color photographic photosensitive material in the presence of a p-phenylenediamine color developing agent represented by the following general formula (I-β):

$$A-(-L-B)_q \qquad (I\text{-}\beta)$$

wherein A represents a p-phenylenediamine color developing agent residue derived from the compound represented by the following formula (II):

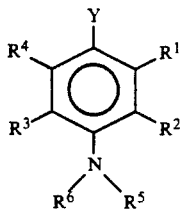

wherein $R^1$, $R^2$, $R^3$ and $R^4$ may be the same or different from one another and each represent a hydrogen atom or a non-metallic substituent, and $R^5$ and $R^6$ may be the same or different and each represent a hydrogen atom or an alkyl, aryl or heterocyclic group, and
Y represents $-NH_2$, $-NHY^1$ or $-N=Y^2$,
$Y^1$ represents $-SO_3H$, $-SO_3Na$, $-SO_2-R^{21}$

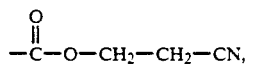

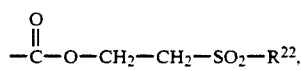

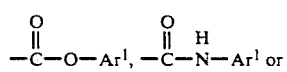

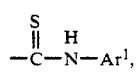

$R^{21}$ and $R^{22}$ may be the same or different and each represent an alkyl group or aryl group, $Ar^1$ represents an aryl group,
$Y^2$ represents

and $Ar^2$ represents an aryl group, and
$R^1$ and $R^2$ and/or $R^2$ and $R^5$ and/or $R^5$ and $R^6$ and/or $R^3$ and $^6R$ and/or $R^3$ and $R^4$ may bond together to form a ring structure,
B represents a monovalent group derived from a compound represented by the following formula (IV):

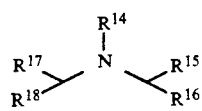

wherein $R^{14}$ represents an alkyl group; $R^{15}$, $R^{16}$, $R^{17}$ and $R^{18}$ may be the same or different from one another and each represent a hydrogen atom, alkyl group or aryl group, and D represents a non-metallic atomic group necessitated for forming a 5- to 7-membered ring, L represents a divalent connecting group or mere bond, q represents an integer of 1 to 3, and when q is 2 or 3, L—B may be the same or different from one another, and B is bonded to A through $R^1$, $R^2$, $R^3$, $R^4$, $R^5$ and $R^6$ and through L.

9. A process for forming an image of claim 8 wherein $R^1$, $R^2$, $R^3$ and $R^4$ each represent a hydrogen atom, halogen atom, amino group, alkyl group, aryl group, heterocyclic group, cyano group, nitro group, hydroxyl group, carboxyl group, alkoxyl group, aryloxy group, acylamino group, alkylamino group, anilino group, ureido group, sulfamoylamino group, alkythio group, arylthio group, alkoxycarbonylamino group, sulfonamido group, carbamoyl group, sulfamoyl group, sulfonyl group, alkoxycarbonyl group, heterocyclic-oxy group, azo group, acyloxy group, carbamoyloxy group, silyl group, silyloxy group, aryloxycarbonylamino group, imido group, heterocyclic thio group, sulfinyl group, phosphonyl group, sulfo group, aryloxycarbonyl group or acyl group.

10. A process for forming an image of claim 8 wherein $R^1$, $R^2$, $R^3$, $R^4$ each represent a hydrogen atom, alkyl, alkoxyl, alkoxycarbonylamine and ureido groups, $R^5$ and $R^6$ each represent a substituted or unsubstituted alkyl group having 1 to 16 carbon atoms, and Y represents $-NH_2$.

11. A process for forming an image of claim 8 wherein B is derived from the compound represented by the following formula (V), (VI) or (VII):

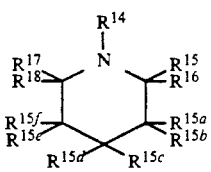

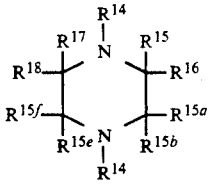

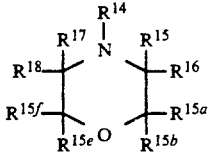

wherein $R^{14}$ and $R^{14'}$ each represent an alkyl group, $R^{15a}$, $R^{15b}$, $R^{15c}$, $R^{15d}$, $R^{15e}$ and $R^{15f}$ may be the same or different from one another and each represent a hydrogen atom or a nonmetallic substituent.

12. A process for forming an image of claim 8 wherein the color developing agent is represented by the following formula (XIII):

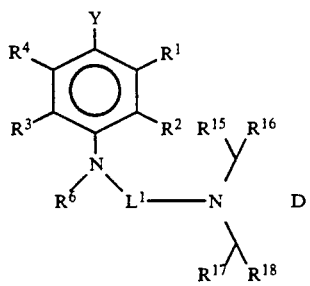

(XIII)

wherein $R^1$, $R^2$, $R^3$ and $R^4$ each represent a hydrogen atom, halogen atom, amino group, alkyl group, aryl group, heterocyclic group, cyano group, nitro group, hydroxyl group, carboxyl group, alkoxyl group, aryloxy group, acylamino group, alkylamino group, anilino group, ureido group, sulfamoylamino group, alkythio group, arylthio group, alkoxycarbonylamino group, sulfonamido group, carbamoyl group, sulfamoyl group, sulfonyl group, alkoxycarbonyl group, heterocyclicoxy group, azo group, acyloxy group, carbamoyloxy group, silyl group, silyloxy group, aryloxycarbonylamino group, imido group, heterocyclic thio group, sulfinyl group, phosphonyl group, sulfo group, aryloxycarbonyl group or acyl group, $R^6$ represents a hydrogen atom or an alkyl, aryl or heterocyclic group, and $R^{15}$, $R^{16}$, $R^{17}$ and $R^{18}$ may be the same or different from one another and each represent a hydrogen atom, alkyl group or aryl group, D represents a non-metallic atomic group necessitated for forming a 5- to 7-membered ring, $L^1$ represents a substituted or unsubstituted alkylene group having 1 to 8 carbon atoms, and Y represents $-NH_2$, $-NHY^1$ or $-N=Y^2$,
$Y^1$ represents $-SO_3H$, $-SO_3Na$, $-SO_2-R^{21}$, $$-\overset{O}{\underset{\|}{C}}-O-CH_2-CH_2-CN,$$

$$-\overset{O}{\underset{\|}{C}}-O-CH_2-CH_2-SO_2-R^{22},$$

$$-\overset{O}{\underset{\|}{C}}-O-Ar^1, -\overset{O}{\underset{\|}{C}}-\overset{H}{\underset{}{N}}-Ar^1 \text{ or}$$

$$-\overset{S}{\underset{\|}{C}}-\overset{H}{\underset{}{N}}-Ar^1,$$

$R^{21}$ and $R^{22}$ may be the same or different and each represent an alkyl group or aryl group, $Ar^1$ represents an aryl group
$Y^2$ represents $$=C\overset{H}{\underset{Ar^2}{\diagdown}},$$

and $Ar^2$ represents an aryl group.

13. A process for forming an image of claim 1 wherein the image-wise exposed photosensitive material is color-developed with a color-developer having a pH of 9 to 12 and containing the p-phenylenediamine color developing agent in an amount of $1\times10^{-3}$ to $1\times10^{-1}$ mol/l at a temperature of 10° to 50° C. for 20 seconds to 10 minutes.

* * * * *